(12) United States Patent
Tiensuu et al.

(10) Patent No.: US 12,379,744 B2
(45) Date of Patent: Aug. 5, 2025

(54) WEARABLE RING DEVICE WITH BATTERY IN COVER

(71) Applicant: Oura Health Oy, Oulu (FI)

(72) Inventors: Ville Tiensuu, Oulu (FI); Mika Törmälä, Oulu (FI)

(73) Assignee: Oura Health Oy, Oulu (FI)

( * ) Notice: Subject to any disclaimer, the term of this patent is extended or adjusted under 35 U.S.C. 154(b) by 266 days.

(21) Appl. No.: 18/320,852

(22) Filed: May 19, 2023

(65) Prior Publication Data
US 2024/0385649 A1 Nov. 21, 2024

(51) Int. Cl.
| | |
|---|---|
| *G06F 1/16* | (2006.01) |
| *A61B 5/00* | (2006.01) |
| *H01M 10/04* | (2006.01) |
| *H01M 10/42* | (2006.01) |
| H01M 50/593 | (2021.01) |

(52) U.S. Cl.
CPC .......... *G06F 1/1635* (2013.01); *A61B 5/6803* (2013.01); *G06F 1/163* (2013.01); *H01M 10/04* (2013.01); *H01M 10/425* (2013.01); *H01M 50/593* (2021.01); *H01M 2220/30* (2013.01)

(58) Field of Classification Search
CPC ........ G06F 1/163; G06F 1/1635; G06F 3/016; G06F 3/017; G06F 3/042; G06F 3/044; H01M 2220/30
USPC ..................................................... 361/679.03
See application file for complete search history.

(56) References Cited

U.S. PATENT DOCUMENTS

| | | | | |
|---|---|---|---|---|
| 5,191,891 | A * | 3/1993 | Righter | A61B 5/332 600/523 |
| 5,490,523 | A * | 2/1996 | Isaacson | A61B 5/6826 600/323 |
| 6,101,843 | A * | 8/2000 | Nagano | A44C 9/003 63/15.3 |
| 6,495,283 | B1 * | 12/2002 | Yoon | H01M 6/18 29/623.5 |
| 7,526,927 | B2 * | 5/2009 | Pinto | A44C 9/00 63/15 |
| 8,346,327 | B2 * | 1/2013 | Campbell | A61B 5/443 600/323 |
| D817,496 | S * | 5/2018 | Stirn | D24/167 |
| 10,366,220 | B2 * | 7/2019 | Shapiro | H04W 12/33 |
| 10,412,558 | B2 * | 9/2019 | Prencipe | H04W 4/21 |
| 10,459,495 | B2 * | 10/2019 | Griffin | G06F 3/03547 |
| 11,360,587 | B1 * | 6/2022 | Wang | G06F 3/016 |

(Continued)

*Primary Examiner* — Adrian S Wilson
(74) *Attorney, Agent, or Firm* — Holland & Hart LLP

(57) ABSTRACT

Methods of manufacturing and devices for a wearable ring device with a battery in the cover of the device are described. The wearable ring device includes an outer shell component with an inner circumferential surface. The battery may extend radially around at least a portion of a circumference of the wearable ring device. In some cases, the wearable ring device may include a battery chamber configured to enclose the battery and charge carriers. One or more structural boundaries of the battery chamber are formed by a cavity within the inner circumferential surface and a battery cover layer coupled to the inner circumferential surface. The wearable ring device may include a printed circuit board (PCB) including a plurality of sensors electrically coupled to the battery. The PCB overlaps with the battery for at least a portion of the circumference of the wearable ring device.

20 Claims, 7 Drawing Sheets

(56) References Cited

U.S. PATENT DOCUMENTS

| | | | | |
|---|---|---|---|---|
| 12,177,997 | B2* | 12/2024 | Doval | H04B 5/72 |
| 2003/0142065 | A1* | 7/2003 | Pahlavan | G06F 3/0346 |
| | | | | 345/156 |
| 2010/0100004 | A1* | 4/2010 | van Someren | A61B 5/4818 |
| | | | | 600/595 |
| 2011/0070480 | A1* | 3/2011 | Hahn | H01M 6/40 |
| | | | | 29/623.5 |
| 2012/0218184 | A1* | 8/2012 | Wissmar | G06F 3/0346 |
| | | | | 345/158 |
| 2013/0108907 | A1* | 5/2013 | Bhardwaj | H01M 10/0431 |
| | | | | 29/623.2 |
| 2015/0062086 | A1* | 3/2015 | Nattukallingal | G06F 3/016 |
| | | | | 345/175 |
| 2015/0220109 | A1* | 8/2015 | von Badinski | G06V 40/70 |
| | | | | 368/10 |
| 2015/0349556 | A1* | 12/2015 | Mercando | H02J 7/32 |
| | | | | 455/573 |
| 2017/0235933 | A1* | 8/2017 | von Badinski | H02J 7/35 |
| | | | | 726/19 |
| 2023/0376071 | A1* | 11/2023 | von Badinski | G02B 19/0052 |
| 2025/0064396 | A1* | 2/2025 | Järvelä | A61B 5/6802 |

* cited by examiner

WEARABLE RING DEVICE WITH BATTERY IN COVER

FIELD OF TECHNOLOGY

The following relates to wearable devices and data processing, including a wearable ring device with a battery in the cover of the device.

BACKGROUND

Some wearable devices may be configured to collect data from users, including heart rate, motion data, temperature data, photoplethysmogram (PPG) data, and the like. In some cases, some wearable devices may perform various actions, such as providing certain health insights to users and based on acquired physiological data in order to assist the user with improving their overall health. Wearable devices may include a battery configured to power the one or more sensors in order to collect the physiological data from the users. However, there is a desire to make wearable devices smaller and more compact to make the wearable devices more comfortable for the user, which imposes size and geometric constraints on the battery.

DETAILED DESCRIPTION

Figure 1:
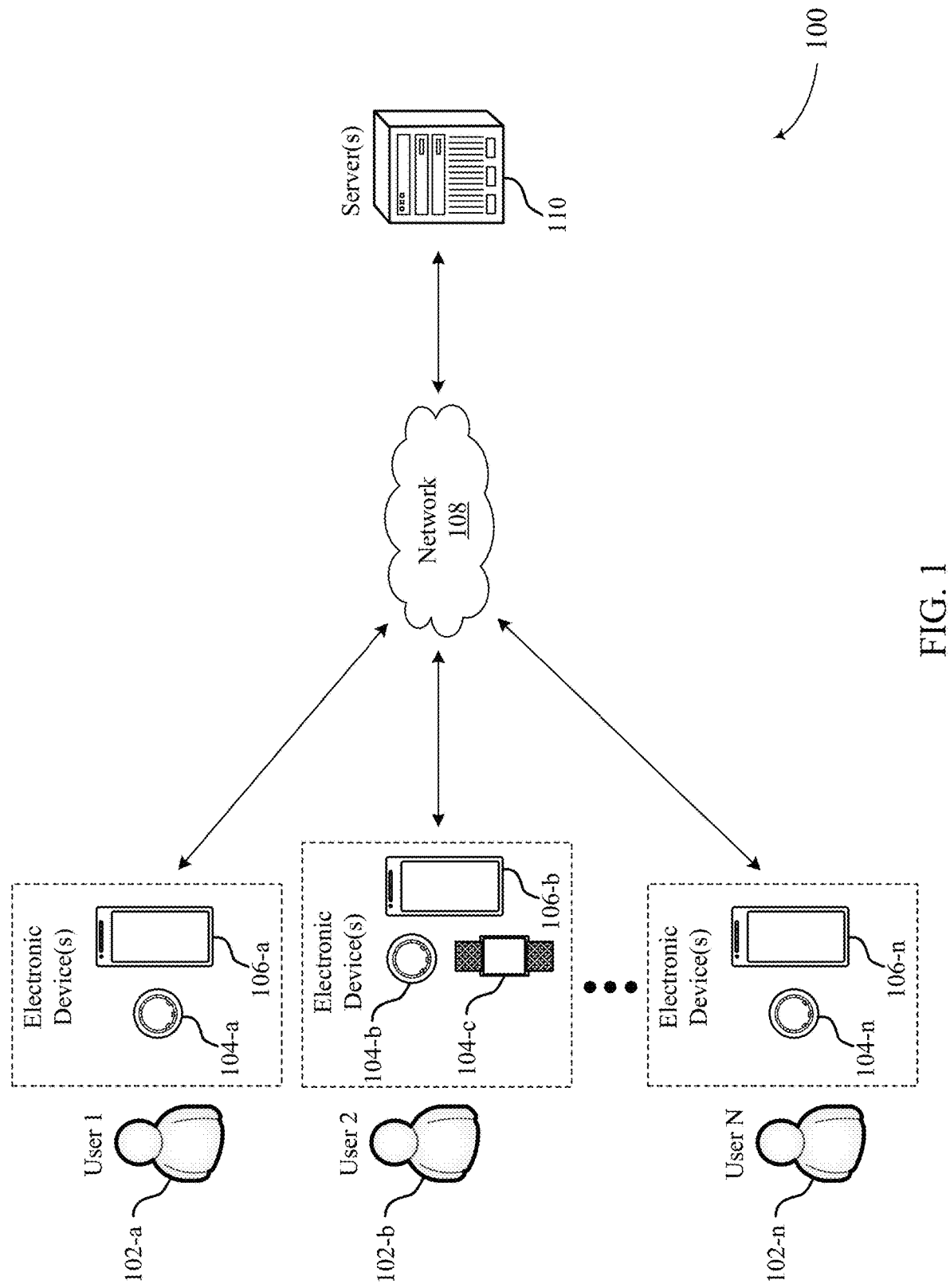
FIG. 1 illustrates an example of a system that supports a wearable ring device with a battery in the cover of the device in accordance with aspects of the present disclosure.

In some wearable devices, the size of the battery may be the main limiting factor for the overall size of the wearable device, as well as the geometric arrangement of components within the wearable device. Such size and geometric constraints may be prominent in wearable devices with smaller form factors, such as rings. For example, in some wearable ring devices, the battery may take up almost the entire width of the ring, and may span radially around a large portion of the circumference of the ring (e.g., the battery may span 140° around the ring). In such cases, the thickness of the battery may be made of multiple anode layers and cathode layers and walls of a battery housing (e.g., an aluminum pouch) that contains the anode/cathode layers and charge carriers (e.g., electrolyte fluid).

To prevent further increasing the thickness of the ring, other components and sensors may be positioned at other radial positions around the ring. In some cases, the thickness of the battery may prevent the ability of other sensors to be positioned on top of the battery, as doing so would make the wearable device too bulky and uncomfortable to wear. In such cases, because sensors cannot be placed on top of the battery due to the thickness of the battery, the position of other sensors may be restricted to the remaining portion of the circumference of the ring that is unoccupied by the battery (e.g., if the battery 140° around the circumference of the ring, the sensors may be limited to the remaining 220°). Such a limitation restricts the quantity and variation of optical channels usable for measurements. Moreover, restricting sensor arrangements to portions of the circumference of the ring may result in the ring being unable to perform measurements when the ring is inadvertently rotated on the user's finger.

Accordingly, to facilitate smaller form-factor wearable devices and therefore improved user experience for users of the wearable devices, aspects of the present disclosure are directed to wearable devices with a battery in the cover of the wearable device. In some implementations, a structure and arrangement of a wearable ring device may include a battery that is partially built into the outer shell of the wearable ring device. In particular, the outer shell of a wearable ring device may form part of the walls for a battery chamber that houses the anode/cathode layers and charge carriers (e.g., electrolyte fluid) of the ring, thereby reducing the need for dedicated battery housing walls and reducing the overall thickness of the battery. In other words, the outer shell of the ring may be "re-used" or "re-purposed" as part of the boundaries of the battery. Moreover, by building the battery into the outer shell, the battery may be made thinner, thereby enabling sensors to be placed on top of the battery. As such, the battery may therefore span up to 360° around the full circumference of the ring, thereby increasing the radial footprint of the battery, reducing the quantity of layers required to achieve the same battery performance as compared to other conventional ring batteries, and further decreasing the thickness of the battery.

For example, the wearable ring device may include an outer shell that includes an inner circumferential surface and an outer circumferential surface. The wearable ring device may include a battery that extends radially around the circumference of the wearable ring device. The inner circumferential surface of the outer shell may form part of the walls for a battery chamber that encloses the set of anode and cathode layers of the battery and electrolyte fluid. In such cases, the battery housing walls may include the inner circumferential surface of the outer shell and a battery cover layer that is coupled to the inner circumferential surface such that the battery chamber forms a liquid-tight enclosure. The wearable ring device may further include a printed circuit board (PCB) that includes the sensors configured to acquire physiological data. The PCB may overlap with the battery for at least a portion of the circumference of the wearable ring device.

In some cases, reducing the thickness of the battery may alleviate spatial and structural constraints on the placement of sensors around the wearable ring device. In particular, reducing the battery thickness (e.g., by using the outer shell as a wall of the battery chamber, and reducing the quantity of layers by spanning the battery further around the ring circumference) may enable the sensors (e.g., the PCB) to be placed on top of (e.g., overlap with) the battery. As such, techniques described herein may enable sensors to be placed on top of the battery, and up to 360° around the full circumference of the ring, thereby increasing the quantity and variation of optical channels, and making the ring more robust to rotation (e.g., enabling the ring to perform physiological measurements regardless of the relative rotation of the ring).

Aspects of the disclosure are initially described in the context of systems supporting physiological data collection from users via wearable devices. Aspects are then described in the context of wearable ring devices and a process flow diagram. Aspects of the disclosure are further illustrated by and described with reference to a system diagram and a flowchart that relate to a wearable ring device with a battery in the cover of the device.

FIG. 1 illustrates an example of a system 100 that supports a wearable ring device with a battery in the cover of the device in accordance with aspects of the present disclosure. The system 100 includes a plurality of electronic devices (e.g., wearable devices 104, user devices 106) that may be worn and/or operated by one or more users 102. The system 100 further includes a network 108 and one or more servers 110.

The electronic devices may include any electronic devices known in the art, including wearable devices 104 (e.g., ring wearable devices, watch wearable devices, etc.), user devices 106 (e.g., smartphones, laptops, tablets). The electronic devices associated with the respective users 102 may include one or more of the following functionalities: 1) measuring physiological data, 2) storing the measured data, 3) processing the data, 4) providing outputs (e.g., via GUIs) to a user 102 based on the processed data, and 5) communicating data with one another and/or other computing devices. Different electronic devices may perform one or more of the functionalities.

Example wearable devices 104 may include wearable computing devices, such as a ring computing device (hereinafter "ring") configured to be worn on a user's 102 finger, a wrist computing device (e.g., a smart watch, fitness band, or bracelet) configured to be worn on a user's 102 wrist, and/or a head mounted computing device (e.g., glasses/goggles). Wearable devices 104 may also include bands, straps (e.g., flexible or inflexible bands or straps), stick-on sensors, and the like, that may be positioned in other locations, such as bands around the head (e.g., a forehead headband), arm (e.g., a forearm band and/or bicep band), and/or leg (e.g., a thigh or calf band), behind the ear, under the armpit, and the like. Wearable devices 104 may also be attached to, or included in, articles of clothing. For example, wearable devices 104 may be included in pockets and/or pouches on clothing. As another example, wearable device 104 may be clipped and/or pinned to clothing, or may otherwise be maintained within the vicinity of the user 102. Example articles of clothing may include, but are not limited to, hats, shirts, gloves, pants, socks, outerwear (e.g., jackets), and undergarments. In some implementations, wearable devices 104 may be included with other types of devices such as training/sporting devices that are used during physical activity. For example, wearable devices 104 may be attached to, or included in, a bicycle, skis, a tennis racket, a golf club, and/or training weights.

Much of the present disclosure may be described in the context of a ring wearable device 104. Accordingly, the terms "ring 104," "wearable device 104," and like terms, may be used interchangeably, unless noted otherwise herein. However, the use of the term "ring 104" is not to be regarded as limiting, as it is contemplated herein that aspects of the present disclosure may be performed using other wearable devices (e.g., watch wearable devices, necklace wearable device, bracelet wearable devices, earring wearable devices, anklet wearable devices, and the like).

In some aspects, user devices 106 may include handheld mobile computing devices, such as smartphones and tablet computing devices. User devices 106 may also include personal computers, such as laptop and desktop computing devices. Other example user devices 106 may include server computing devices that may communicate with other electronic devices (e.g., via the Internet). In some implementations, computing devices may include medical devices, such as external wearable computing devices (e.g., Holter monitors). Medical devices may also include implantable medical devices, such as pacemakers and cardioverter defibrillators. Other example user devices 106 may include home computing devices, such as internet of things (IoT) devices (e.g., IoT devices), smart televisions, smart speakers, smart displays (e.g., video call displays), hubs (e.g., wireless communication hubs), security systems, smart appliances (e.g., thermostats and refrigerators), and fitness equipment.

Some electronic devices (e.g., wearable devices 104, user devices 106) may measure physiological parameters of respective users 102, such as photoplethysmography waveforms, continuous skin temperature, a pulse waveform, respiration rate, heart rate, heart rate variability (HRV), actigraphy, galvanic skin response, pulse oximetry, blood oxygen saturation (SpO2), blood sugar levels (e.g., glucose metrics), and/or other physiological parameters. Some electronic devices that measure physiological parameters may also perform some/all of the calculations described herein. Some electronic devices may not measure physiological parameters, but may perform some/all of the calculations described herein. For example, a ring (e.g., wearable device 104), mobile device application, or a server computing device may process received physiological data that was measured by other devices.

In some implementations, a user 102 may operate, or may be associated with, multiple electronic devices, some of which may measure physiological parameters and some of which may process the measured physiological parameters. In some implementations, a user 102 may have a ring (e.g., wearable device 104) that measures physiological parameters. The user 102 may also have, or be associated with, a user device 106 (e.g., mobile device, smartphone), where the wearable device 104 and the user device 106 are communicatively coupled to one another. In some cases, the user device 106 may receive data from the wearable device 104 and perform some/all of the calculations described herein. In some implementations, the user device 106 may also measure physiological parameters described herein, such as motion/activity parameters.

For example, as illustrated in FIG. 1, a first user 102-a (User 1) may operate, or may be associated with, a wearable device 104-a (e.g., ring 104-a) and a user device 106-a that may operate as described herein. In this example, the user device 106-a associated with user 102-a may process/store physiological parameters measured by the ring 104-a. Comparatively, a second user 102-b (User 2) may be associated with a ring 104-b, a watch wearable device 104-c (e.g., watch 104-c), and a user device 106-b, where the user device 106-b associated with user 102-b may process/store physiological parameters measured by the ring 104-b and/or the watch 104-c. Moreover, an nth user 102-n (User N) may be associated with an arrangement of electronic devices described herein (e.g., ring 104-n, user device 106-n). In some aspects, wearable devices 104 (e.g., rings 104, watches 104) and other electronic devices may be communicatively coupled to the user devices 106 of the respective users 102 via Bluetooth, Wi-Fi, and other wireless protocols.

In some implementations, the rings 104 (e.g., wearable devices 104) of the system 100 may be configured to collect physiological data from the respective users 102 based on arterial blood flow within the user's finger. In particular, a ring 104 may utilize one or more light-emitting components, such as LEDs (e.g., red LEDs, green LEDs) that emit light on the palm-side of a user's finger to collect physiological data based on arterial blood flow within the user's finger. In general, the terms light-emitting components, light-emitting elements, and like terms, may include, but are not limited to, LEDs, micro LEDs, mini LEDs, laser diodes (LDs) (e.g., vertical cavity surface-emitting lasers (VCSELs), and the like.

In some cases, the system 100 may be configured to collect physiological data from the respective users 102 based on blood flow diffused into a microvascular bed of skin with capillaries and arterioles. For example, the system 100 may collect PPG data based on a measured amount of blood diffused into the microvascular system of capillaries and arterioles. In some implementations, the ring 104 may acquire the physiological data using a combination of both green and red LEDs. The physiological data may include any physiological data known in the art including, but not limited to, temperature data, accelerometer data (e.g., movement/motion data), heart rate data, HRV data, blood oxygen level data, or any combination thereof.

The use of both green and red LEDs may provide several advantages over other solutions, as red and green LEDs have been found to have their own distinct advantages when acquiring physiological data under different conditions (e.g., light/dark, active/inactive) and via different parts of the body, and the like. For example, green LEDs have been found to exhibit better performance during exercise. Moreover, using multiple LEDs (e.g., green and red LEDs) distributed around the ring 104 has been found to exhibit superior performance as compared to wearable devices that utilize LEDs that are positioned close to one another, such as within a watch wearable device. Furthermore, the blood vessels in the finger (e.g., arteries, capillaries) are more accessible via LEDs as compared to blood vessels in the wrist. In particular, arteries in the wrist are positioned on the bottom of the wrist (e.g., palm-side of the wrist), meaning only capillaries are accessible on the top of the wrist (e.g., back of hand side of the wrist), where wearable watch devices and similar devices are typically worn. As such, utilizing LEDs and other sensors within a ring 104 has been found to exhibit superior performance as compared to wearable devices worn on the wrist, as the ring 104 may have greater access to arteries (as compared to capillaries), thereby resulting in stronger signals and more valuable physiological data.

The electronic devices of the system 100 (e.g., user devices 106, wearable devices 104) may be communicatively coupled to one or more servers 110 via wired or wireless communication protocols. For example, as shown in FIG. 1, the electronic devices (e.g., user devices 106) may be communicatively coupled to one or more servers 110 via a network 108. The network 108 may implement transfer control protocol and internet protocol (TCP/IP), such as the Internet, or may implement other network 108 protocols. Network connections between the network 108 and the respective electronic devices may facilitate transport of data via email, web, text messages, mail, or any other appropriate form of interaction within a computer network 108. For example, in some implementations, the ring 104-*a* associated with the first user 102-*a* may be communicatively coupled to the user device 106-*a*, where the user device 106-*a* is communicatively coupled to the servers 110 via the network 108. In additional or alternative cases, wearable devices 104 (e.g., rings 104, watches 104) may be directly communicatively coupled to the network 108.

The system 100 may offer an on-demand database service between the user devices 106 and the one or more servers 110. In some cases, the servers 110 may receive data from the user devices 106 via the network 108, and may store and analyze the data. Similarly, the servers 110 may provide data to the user devices 106 via the network 108. In some cases, the servers 110 may be located at one or more data centers. The servers 110 may be used for data storage, management, and processing. In some implementations, the servers 110 may provide a web-based interface to the user device 106 via web browsers.

In some aspects, the system 100 may detect periods of time that a user 102 is asleep, and classify periods of time that the user 102 is asleep into one or more sleep stages (e.g., sleep stage classification). For example, as shown in FIG. 1, User 102-*a* may be associated with a wearable device 104-*a* (e.g., ring 104-*a*) and a user device 106-*a*. In this example, the ring 104-*a* may collect physiological data associated with the user 102-*a*, including temperature, heart rate, HRV, respiratory rate, and the like. In some aspects, data collected by the ring 104-*a* may be input to a machine learning classifier, where the machine learning classifier is configured to determine periods of time that the user 102-*a* is (or was) asleep. Moreover, the machine learning classifier may be configured to classify periods of time into different sleep stages, including an awake sleep stage, a rapid eye movement (REM) sleep stage, a light sleep stage (non-REM (NREM)), and a deep sleep stage (NREM). In some aspects, the classified sleep stages may be displayed to the user 102-*a* via a GUI of the user device 106-*a*. Sleep stage classification may be used to provide feedback to a user 102-*a* regarding the user's sleeping patterns, such as recommended bedtimes, recommended wake-up times, and the like. Moreover, in some implementations, sleep stage classification techniques described herein may be used to calculate scores for the respective user, such as Sleep Scores, Readiness Scores, and the like.

In some aspects, the system 100 may utilize circadian rhythm-derived features to further improve physiological data collection, data processing procedures, and other techniques described herein. The term circadian rhythm may refer to a natural, internal process that regulates an individual's sleep-wake cycle, that repeats approximately every 24 hours. In this regard, techniques described herein may utilize circadian rhythm adjustment models to improve physiological data collection, analysis, and data processing. For example, a circadian rhythm adjustment model may be input into a machine learning classifier along with physiological data collected from the user 102-*a* via the wearable device 104-*a*. In this example, the circadian rhythm adjustment model may be configured to "weight," or adjust, physiological data collected throughout a user's natural, approximately 24-hour circadian rhythm. In some implementations, the system may initially start with a "baseline" circadian rhythm adjustment model, and may modify the baseline model using physiological data collected from each user 102 to generate tailored, individualized circadian rhythm adjustment models that are specific to each respective user 102.

In some aspects, the system 100 may utilize other biological rhythms to further improve physiological data collection, analysis, and processing by phase of these other rhythms. For example, if a weekly rhythm is detected within an individual's baseline data, then the model may be configured to adjust "weights" of data by day of the week. Biological rhythms that may require adjustment to the model by this method include: 1) ultradian (faster than a day rhythms, including sleep cycles in a sleep state, and oscillations from less than an hour to several hours periodicity in the measured physiological variables during wake state; 2) circadian rhythms; 3) non-endogenous daily rhythms shown to be imposed on top of circadian rhythms, as in work schedules; 4) weekly rhythms, or other artificial time periodicities exogenously imposed (e.g. in a hypothetical culture with 12 day "weeks," 12 day rhythms could be used); 5) multi-day ovarian rhythms in women and spermatogenesis rhythms in men; 6) lunar rhythms (relevant for individuals living with low or no artificial lights); and 7) seasonal rhythms.

The biological rhythms are not always stationary rhythms. For example, many women experience variability in ovarian cycle length across cycles, and ultradian rhythms are not expected to occur at exactly the same time or periodicity across days even within a user. As such, signal processing techniques sufficient to quantify the frequency composition while preserving temporal resolution of these rhythms in physiological data may be used to improve detection of these rhythms, to assign phase of each rhythm to each moment in time measured, and to thereby modify adjustment models and comparisons of time intervals. The biological rhythm-adjustment models and parameters can be added in linear or non-linear combinations as appropriate to more accurately capture the dynamic physiological baselines of an individual or group of individuals.

In some aspects, the respective devices of the system 100 may support techniques for implementing a battery in the cover of a wearable device (e.g., wearable device 104). The battery may be integrated into an outer shell (e.g., the cover) of the wearable device 104 and may incorporate additional and/or update existing functionality of the wearable device 104. For example, the battery may extend radially around at least a portion of a circumference of the wearable device 104. In such cases, a radial footprint of the battery may increase and a thickness of the battery may decrease as the quantity of layers required to achieve the same battery performance is reduced as compared to other conventional wearable device batteries.

The wearable device 104 may include the outer shell that includes an inner circumferential surface and an outer circumferential surface. The battery of the wearable device 104 may include a set of anode and cathode layers. In some cases, the set of anode and cathode layers and an electrolyte fluid may be enclosed by a battery chamber. The battery chamber may be formed by a cavity within the inner circumferential surface of the outer shell and a battery cover layer that is coupled to the inner circumferential surface to form an aluminum pouch. In such cases, the external housing of the wearable device 104 and the battery share a common outer cover (e.g., outer circumferential surface).

The wearable device 104 may further include a flexible PCB that includes one or more sensors. The sensors may be electrically coupled to the battery and configured to acquire physiological data. In some cases, the flexible PCB may overlap with the battery for at least a portion of the circumference of the wearable device 104. In such cases, the quantity and variation of optical channels may increase as the sensors may be placed on top of the battery and span up to a full circumference of the wearable device 104. For example, the measurement points for electronics and optics may be arranged around the entire circumference of the ring, thereby improving the quality of the measurements as the measurements may not be as sensitive to rotation.

It should be appreciated by a person skilled in the art that one or more aspects of the disclosure may be implemented in a system 100 to additionally or alternatively solve other problems than those described above. Furthermore, aspects of the disclosure may provide technical improvements to "conventional" systems or processes as described herein. However, the description and appended drawings only include example technical improvements resulting from implementing aspects of the disclosure, and accordingly do not represent all of the technical improvements provided within the scope of the claims.

Figure 2:
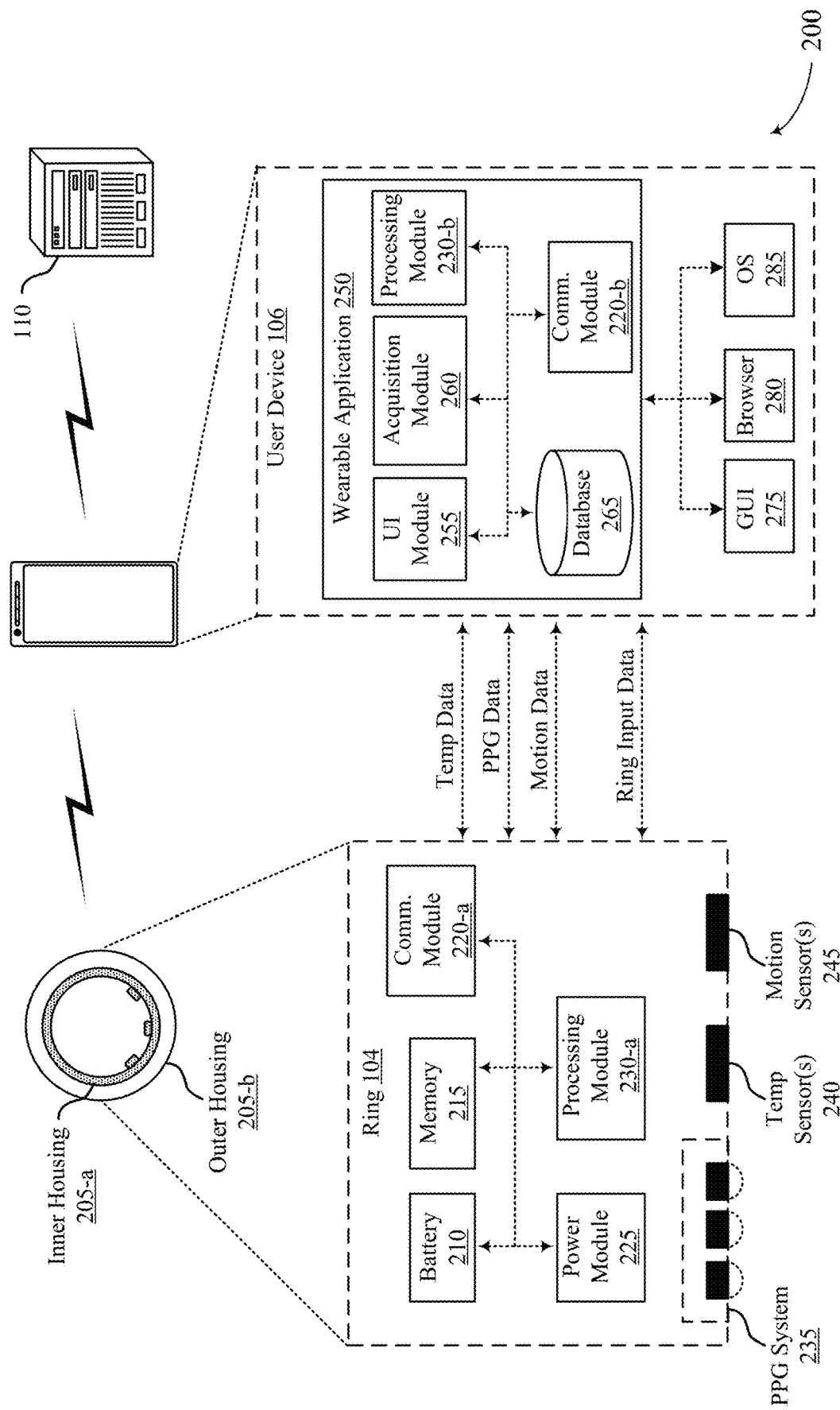
FIG. 2 illustrates an example of a system that supports a wearable ring device with a battery in the cover of the device in accordance with aspects of the present disclosure.

FIG. 2 illustrates an example of a system 200 that supports a wearable ring device with a battery in the cover of the device in accordance with aspects of the present disclosure. The system 200 may implement, or be implemented by, system 100. In particular, system 200 illustrates an example of a ring 104 (e.g., wearable device 104), a user device 106, and a server 110, as described with reference to FIG. 1.

In some aspects, the ring 104 may be configured to be worn around a user's finger, and may determine one or more user physiological parameters when worn around the user's finger. Example measurements and determinations may include, but are not limited to, user skin temperature, pulse waveforms, respiratory rate, heart rate, HRV, blood oxygen levels (SpO2), blood sugar levels (e.g., glucose metrics), and the like.

The system 200 further includes a user device 106 (e.g., a smartphone) in communication with the ring 104. For example, the ring 104 may be in wireless and/or wired communication with the user device 106. In some implementations, the ring 104 may send measured and processed data (e.g., temperature data, photoplethysmogram (PPG) data, motion/accelerometer data, ring input data, and the like) to the user device 106. The user device 106 may also send data to the ring 104, such as ring 104 firmware/configuration updates. The user device 106 may process data. In some implementations, the user device 106 may transmit data to the server 110 for processing and/or storage.

The ring 104 may include a housing 205 that may include an inner housing 205-a and an outer housing 205-b. In some aspects, the housing 205 of the ring 104 may store or otherwise include various components of the ring including, but not limited to, device electronics, a power source (e.g., battery 210, and/or capacitor), one or more substrates (e.g., printable circuit boards) that interconnect the device electronics and/or power source, and the like. The device electronics may include device modules (e.g., hardware/software), such as: a processing module 230-a, a memory 215, a communication module 220-a, a power module 225, and the like. The device electronics may also include one or more sensors. Example sensors may include one or more temperature sensors 240, a PPG sensor assembly (e.g., PPG system 235), and one or more motion sensors 245.

The sensors may include associated modules (not illustrated) configured to communicate with the respective components/modules of the ring 104, and generate signals associated with the respective sensors. In some aspects, each of the components/modules of the ring 104 may be communicatively coupled to one another via wired or wireless connections. Moreover, the ring 104 may include additional and/or alternative sensors or other components that are configured to collect physiological data from the user, including light sensors (e.g., LEDs), oximeters, and the like.

The ring 104 shown and described with reference to FIG. 2 is provided solely for illustrative purposes. As such, the ring 104 may include additional or alternative components as those illustrated in FIG. 2. Other rings 104 that provide functionality described herein may be fabricated. For example, rings 104 with fewer components (e.g., sensors) may be fabricated. In a specific example, a ring 104 with a single temperature sensor 240 (or other sensor), a power source, and device electronics configured to read the single temperature sensor 240 (or other sensor) may be fabricated. In another specific example, a temperature sensor 240 (or other sensor) may be attached to a user's finger (e.g., using a clamps, spring loaded clamps, etc.). In this case, the sensor may be wired to another computing device, such as a wrist worn computing device that reads the temperature sensor 240 (or other sensor). In other examples, a ring 104 that includes additional sensors and processing functionality may be fabricated.

The housing 205 may include one or more housing 205 components. The housing 205 may include an outer housing 205-b component (e.g., a shell) and an inner housing 205-a component (e.g., a molding). The housing 205 may include additional components (e.g., additional layers) not explicitly illustrated in FIG. 2. For example, in some implementations, the ring 104 may include one or more insulating layers that electrically insulate the device electronics and other conductive materials (e.g., electrical traces) from the outer housing 205-b (e.g., a metal outer housing 205-b). The housing 205 may provide structural support for the device electronics, battery 210, substrate(s), and other components. For example, the housing 205 may protect the device electronics, battery 210, and substrate(s) from mechanical forces, such as pressure and impacts. The housing 205 may also protect the device electronics, battery 210, and substrate(s) from water and/or other chemicals.

The outer housing 205-b may be fabricated from one or more materials. In some implementations, the outer housing 205-b may include a metal, such as titanium, that may provide strength and abrasion resistance at a relatively light weight. The outer housing 205-b may also be fabricated from other materials, such polymers. In some implementations, the outer housing 205-b may be protective as well as decorative.

The inner housing 205-a may be configured to interface with the user's finger. The inner housing 205-a may be formed from a polymer (e.g., a medical grade polymer) or other material. In some implementations, the inner housing 205-a may be transparent. For example, the inner housing 205-a may be transparent to light emitted by the PPG light emitting diodes (LEDs). In some implementations, the inner housing 205-a component may be molded onto the outer housing 205-b. For example, the inner housing 205-a may include a polymer that is molded (e.g., injection molded) to fit into an outer housing 205-b metallic shell.

The ring 104 may include one or more substrates (not illustrated). The device electronics and battery 210 may be included on the one or more substrates. For example, the device electronics and battery 210 may be mounted on one or more substrates. Example substrates may include one or more PCBs, such as flexible PCB (e.g., polyimide). In some implementations, the electronics/battery 210 may include surface mounted devices (e.g., surface-mount technology (SMT) devices) on a flexible PCB. In some implementations, the one or more substrates (e.g., one or more flexible PCBs) may include electrical traces that provide electrical communication between device electronics. The electrical traces may also connect the battery 210 to the device electronics.

The device electronics, battery 210, and substrates may be arranged in the ring 104 in a variety of ways. In some implementations, one substrate that includes device electronics may be mounted along the bottom of the ring 104 (e.g., the bottom half), such that the sensors (e.g., PPG system 235, temperature sensors 240, motion sensors 245, and other sensors) interface with the underside of the user's finger. In these implementations, the battery 210 may be included along the top portion of the ring 104 (e.g., on another substrate).

The various components/modules of the ring 104 represent functionality (e.g., circuits and other components) that may be included in the ring 104. Modules may include any discrete and/or integrated electronic circuit components that implement analog and/or digital circuits capable of producing the functions attributed to the modules herein. For example, the modules may include analog circuits (e.g., amplification circuits, filtering circuits, analog/digital conversion circuits, and/or other signal conditioning circuits). The modules may also include digital circuits (e.g., combinational or sequential logic circuits, memory circuits etc.).

The memory 215 (memory module) of the ring 104 may include any volatile, non-volatile, magnetic, or electrical media, such as a random access memory (RAM), read-only memory (ROM), non-volatile RAM (NVRAM), electrically-erasable programmable ROM (EEPROM), flash memory, or any other memory device. The memory 215 may store any of the data described herein. For example, the memory 215 may be configured to store data (e.g., motion data, temperature data, PPG data) collected by the respective sensors and PPG system 235. Furthermore, memory 215 may include instructions that, when executed by one or more processing circuits, cause the modules to perform various functions attributed to the modules herein. The device electronics of the ring 104 described herein are only example device electronics. As such, the types of electronic components used to implement the device electronics may vary based on design considerations.

The functions attributed to the modules of the ring 104 described herein may be embodied as one or more processors, hardware, firmware, software, or any combination thereof. Depiction of different features as modules is intended to highlight different functional aspects and does not necessarily imply that such modules must be realized by separate hardware/software components. Rather, functionality associated with one or more modules may be performed by separate hardware/software components or integrated within common hardware/software components.

The processing module 230-a of the ring 104 may include one or more processors (e.g., processing units), microcontrollers, digital signal processors, systems on a chip (SOCs), and/or other processing devices. The processing module 230-a communicates with the modules included in the ring 104. For example, the processing module 230-a may transmit/receive data to/from the modules and other components of the ring 104, such as the sensors. As described herein, the modules may be implemented by various circuit components. Accordingly, the modules may also be referred to as circuits (e.g., a communication circuit and power circuit).

The processing module 230-a may communicate with the memory 215. The memory 215 may include computer-readable instructions that, when executed by the processing module 230-a, cause the processing module 230-a to perform the various functions attributed to the processing module 230-*a* herein. In some implementations, the processing module 230-*a* (e.g., a microcontroller) may include additional features associated with other modules, such as communication functionality provided by the communication module 220-*a* (e.g., an integrated Bluetooth Low Energy transceiver) and/or additional onboard memory 215.

The communication module 220-*a* may include circuits that provide wireless and/or wired communication with the user device 106 (e.g., communication module 220-*b* of the user device 106). In some implementations, the communication modules 220-*a*, 220-*b* may include wireless communication circuits, such as Bluetooth circuits and/or Wi-Fi circuits. In some implementations, the communication modules 220-*a*, 220-*b* can include wired communication circuits, such as Universal Serial Bus (USB) communication circuits. Using the communication module 220-*a*, the ring 104 and the user device 106 may be configured to communicate with each other. The processing module 230-*a* of the ring may be configured to transmit/receive data to/from the user device 106 via the communication module 220-*a*. Example data may include, but is not limited to, motion data, temperature data, pulse waveforms, heart rate data, HRV data, PPG data, and status updates (e.g., charging status, battery charge level, and/or ring 104 configuration settings). The processing module 230-*a* of the ring may also be configured to receive updates (e.g., software/firmware updates) and data from the user device 106.

The ring 104 may include a battery 210 (e.g., a rechargeable battery 210). An example battery 210 may include a Lithium-Ion or Lithium-Polymer type battery 210, although a variety of battery 210 options are possible. The battery 210 may be wirelessly charged. In some implementations, the ring 104 may include a power source other than the battery 210, such as a capacitor. The power source (e.g., battery 210 or capacitor) may have a curved geometry that matches the curve of the ring 104. In some aspects, a charger or other power source may include additional sensors that may be used to collect data in addition to, or that supplements, data collected by the ring 104 itself. Moreover, a charger or other power source for the ring 104 may function as a user device 106, in which case the charger or other power source for the ring 104 may be configured to receive data from the ring 104, store and/or process data received from the ring 104, and communicate data between the ring 104 and the servers 110.

In some aspects, the ring 104 includes a power module 225 that may control charging of the battery 210. For example, the power module 225 may interface with an external wireless charger that charges the battery 210 when interfaced with the ring 104. The charger may include a datum structure that mates with a ring 104 datum structure to create a specified orientation with the ring 104 during charging. The power module 225 may also regulate voltage (s) of the device electronics, regulate power output to the device electronics, and monitor the state of charge of the battery 210. In some implementations, the battery 210 may include a protection circuit module (PCM) that protects the battery 210 from high current discharge, over voltage during charging, and under voltage during discharge. The power module 225 may also include electro-static discharge (ESD) protection.

The one or more temperature sensors 240 may be electrically coupled to the processing module 230-*a*. The temperature sensor 240 may be configured to generate a temperature signal (e.g., temperature data) that indicates a temperature read or sensed by the temperature sensor 240.

The processing module 230-*a* may determine a temperature of the user in the location of the temperature sensor 240. For example, in the ring 104, temperature data generated by the temperature sensor 240 may indicate a temperature of a user at the user's finger (e.g., skin temperature). In some implementations, the temperature sensor 240 may contact the user's skin. In other implementations, a portion of the housing 205 (e.g., the inner housing 205-*a*) may form a barrier (e.g., a thin, thermally conductive barrier) between the temperature sensor 240 and the user's skin. In some implementations, portions of the ring 104 configured to contact the user's finger may have thermally conductive portions and thermally insulative portions. The thermally conductive portions may conduct heat from the user's finger to the temperature sensors 240. The thermally insulative portions may insulate portions of the ring 104 (e.g., the temperature sensor 240) from ambient temperature.

In some implementations, the temperature sensor 240 may generate a digital signal (e.g., temperature data) that the processing module 230-*a* may use to determine the temperature. As another example, in cases where the temperature sensor 240 includes a passive sensor, the processing module 230-*a* (or a temperature sensor 240 module) may measure a current/voltage generated by the temperature sensor 240 and determine the temperature based on the measured current/voltage. Example temperature sensors 240 may include a thermistor, such as a negative temperature coefficient (NTC) thermistor, or other types of sensors including resistors, transistors, diodes, and/or other electrical/electronic components.

The processing module 230-*a* may sample the user's temperature over time. For example, the processing module 230-*a* may sample the user's temperature according to a sampling rate. An example sampling rate may include one sample per second, although the processing module 230-*a* may be configured to sample the temperature signal at other sampling rates that are higher or lower than one sample per second. In some implementations, the processing module 230-*a* may sample the user's temperature continuously throughout the day and night. Sampling at a sufficient rate (e.g., one sample per second) throughout the day may provide sufficient temperature data for analysis described herein.

The processing module 230-*a* may store the sampled temperature data in memory 215. In some implementations, the processing module 230-*a* may process the sampled temperature data. For example, the processing module 230-*a* may determine average temperature values over a period of time. In one example, the processing module 230-*a* may determine an average temperature value each minute by summing all temperature values collected over the minute and dividing by the number of samples over the minute. In a specific example where the temperature is sampled at one sample per second, the average temperature may be a sum of all sampled temperatures for one minute divided by sixty seconds. The memory 215 may store the average temperature values over time. In some implementations, the memory 215 may store average temperatures (e.g., one per minute) instead of sampled temperatures in order to conserve memory 215.

The sampling rate, which may be stored in memory 215, may be configurable. In some implementations, the sampling rate may be the same throughout the day and night. In other implementations, the sampling rate may be changed throughout the day/night. In some implementations, the ring 104 may filter/reject temperature readings, such as large spikes in temperature that are not indicative of physiological changes (e.g., a temperature spike from a hot shower). In some implementations, the ring 104 may filter/reject temperature readings that may not be reliable due to other factors, such as excessive motion during exercise (e.g., as indicated by a motion sensor 245).

The ring 104 (e.g., communication module) may transmit the sampled and/or average temperature data to the user device 106 for storage and/or further processing. The user device 106 may transfer the sampled and/or average temperature data to the server 110 for storage and/or further processing.

Although the ring 104 is illustrated as including a single temperature sensor 240, the ring 104 may include multiple temperature sensors 240 in one or more locations, such as arranged along the inner housing 205-a near the user's finger. In some implementations, the temperature sensors 240 may be stand-alone temperature sensors 240. Additionally, or alternatively, one or more temperature sensors 240 may be included with other components (e.g., packaged with other components), such as with the accelerometer and/or processor.

The processing module 230-a may acquire and process data from multiple temperature sensors 240 in a similar manner described with respect to a single temperature sensor 240. For example, the processing module 230 may individually sample, average, and store temperature data from each of the multiple temperature sensors 240. In other examples, the processing module 230-a may sample the sensors at different rates and average/store different values for the different sensors. In some implementations, the processing module 230-a may be configured to determine a single temperature based on the average of two or more temperatures determined by two or more temperature sensors 240 in different locations on the finger.

The temperature sensors 240 on the ring 104 may acquire distal temperatures at the user's finger (e.g., any finger). For example, one or more temperature sensors 240 on the ring 104 may acquire a user's temperature from the underside of a finger or at a different location on the finger. In some implementations, the ring 104 may continuously acquire distal temperature (e.g., at a sampling rate). Although distal temperature measured by a ring 104 at the finger is described herein, other devices may measure temperature at the same/different locations. In some cases, the distal temperature measured at a user's finger may differ from the temperature measured at a user's wrist or other external body location. Additionally, the distal temperature measured at a user's finger (e.g., a "shell" temperature) may differ from the user's core temperature. As such, the ring 104 may provide a useful temperature signal that may not be acquired at other internal/external locations of the body. In some cases, continuous temperature measurement at the finger may capture temperature fluctuations (e.g., small or large fluctuations) that may not be evident in core temperature. For example, continuous temperature measurement at the finger may capture minute-to-minute or hour-to-hour temperature fluctuations that provide additional insight that may not be provided by other temperature measurements elsewhere in the body.

The ring 104 may include a PPG system 235. The PPG system 235 may include one or more optical transmitters that transmit light. The PPG system 235 may also include one or more optical receivers that receive light transmitted by the one or more optical transmitters. An optical receiver may generate a signal (hereinafter "PPG" signal) that indicates an amount of light received by the optical receiver. The optical transmitters may illuminate a region of the user's finger. The PPG signal generated by the PPG system 235 may indicate the perfusion of blood in the illuminated region. For example, the PPG signal may indicate blood volume changes in the illuminated region caused by a user's pulse pressure. The processing module 230-a may sample the PPG signal and determine a user's pulse waveform based on the PPG signal. The processing module 230-a may determine a variety of physiological parameters based on the user's pulse waveform, such as a user's respiratory rate, heart rate, HRV, oxygen saturation, and other circulatory parameters.

In some implementations, the PPG system 235 may be configured as a reflective PPG system 235 where the optical receiver(s) receive transmitted light that is reflected through the region of the user's finger. In some implementations, the PPG system 235 may be configured as a transmissive PPG system 235 where the optical transmitter(s) and optical receiver(s) are arranged opposite to one another, such that light is transmitted directly through a portion of the user's finger to the optical receiver(s).

The number and ratio of transmitters and receivers included in the PPG system 235 may vary. Example optical transmitters may include light-emitting diodes (LEDs). The optical transmitters may transmit light in the infrared spectrum and/or other spectrums. Example optical receivers may include, but are not limited to, photosensors, phototransistors, and photodiodes. The optical receivers may be configured to generate PPG signals in response to the wavelengths received from the optical transmitters. The location of the transmitters and receivers may vary. Additionally, a single device may include reflective and/or transmissive PPG systems 235.

The PPG system 235 illustrated in FIG. 2 may include a reflective PPG system 235 in some implementations. In these implementations, the PPG system 235 may include a centrally located optical receiver (e.g., at the bottom of the ring 104) and two optical transmitters located on each side of the optical receiver. In this implementation, the PPG system 235 (e.g., optical receiver) may generate the PPG signal based on light received from one or both of the optical transmitters. In other implementations, other placements, combinations, and/or configurations of one or more optical transmitters and/or optical receivers are contemplated.

The processing module 230-a may control one or both of the optical transmitters to transmit light while sampling the PPG signal generated by the optical receiver. In some implementations, the processing module 230-a may cause the optical transmitter with the stronger received signal to transmit light while sampling the PPG signal generated by the optical receiver. For example, the selected optical transmitter may continuously emit light while the PPG signal is sampled at a sampling rate (e.g., 250 Hz).

Sampling the PPG signal generated by the PPG system 235 may result in a pulse waveform that may be referred to as a "PPG." The pulse waveform may indicate blood pressure vs time for multiple cardiac cycles. The pulse waveform may include peaks that indicate cardiac cycles. Additionally, the pulse waveform may include respiratory induced variations that may be used to determine respiration rate. The processing module 230-a may store the pulse waveform in memory 215 in some implementations. The processing module 230-a may process the pulse waveform as it is generated and/or from memory 215 to determine user physiological parameters described herein.

The processing module 230-a may determine the user's heart rate based on the pulse waveform. For example, the processing module 230-a may determine heart rate (e.g., in beats per minute) based on the time between peaks in the pulse waveform. The time between peaks may be referred to as an interbeat interval (IBI). The processing module 230-*a* may store the determined heart rate values and IBI values in memory 215.

The processing module 230-*a* may determine HRV over time. For example, the processing module 230-*a* may determine HRV based on the variation in the IBIs. The processing module 230-*a* may store the HRV values over time in the memory 215. Moreover, the processing module 230-*a* may determine the user's respiratory rate over time. For example, the processing module 230-*a* may determine respiratory rate based on frequency modulation, amplitude modulation, or baseline modulation of the user's IBI values over a period of time. Respiratory rate may be calculated in breaths per minute or as another breathing rate (e.g., breaths per 30 seconds). The processing module 230-*a* may store user respiratory rate values over time in the memory 215.

The ring 104 may include one or more motion sensors 245, such as one or more accelerometers (e.g., 6-D accelerometers) and/or one or more gyroscopes (gyros). The motion sensors 245 may generate motion signals that indicate motion of the sensors. For example, the ring 104 may include one or more accelerometers that generate acceleration signals that indicate acceleration of the accelerometers. As another example, the ring 104 may include one or more gyro sensors that generate gyro signals that indicate angular motion (e.g., angular velocity) and/or changes in orientation. The motion sensors 245 may be included in one or more sensor packages. An example accelerometer/gyro sensor is a Bosch BM1160 inertial micro electro-mechanical system (MEMS) sensor that may measure angular rates and accelerations in three perpendicular axes.

The processing module 230-*a* may sample the motion signals at a sampling rate (e.g., 50 Hz) and determine the motion of the ring 104 based on the sampled motion signals. For example, the processing module 230-*a* may sample acceleration signals to determine acceleration of the ring 104. As another example, the processing module 230-*a* may sample a gyro signal to determine angular motion. In some implementations, the processing module 230-*a* may store motion data in memory 215. Motion data may include sampled motion data as well as motion data that is calculated based on the sampled motion signals (e.g., acceleration and angular values).

The ring 104 may store a variety of data described herein. For example, the ring 104 may store temperature data, such as raw sampled temperature data and calculated temperature data (e.g., average temperatures). As another example, the ring 104 may store PPG signal data, such as pulse waveforms and data calculated based on the pulse waveforms (e.g., heart rate values, IBI values, HRV values, and respiratory rate values). The ring 104 may also store motion data, such as sampled motion data that indicates linear and angular motion.

The ring 104, or other computing device, may calculate and store additional values based on the sampled/calculated physiological data. For example, the processing module 230 may calculate and store various metrics, such as sleep metrics (e.g., a Sleep Score), activity metrics, and readiness metrics. In some implementations, additional values/metrics may be referred to as "derived values." The ring 104, or other computing/wearable device, may calculate a variety of values/metrics with respect to motion. Example derived values for motion data may include, but are not limited to, motion count values, regularity values, intensity values, metabolic equivalence of task values (METs), and orientation values. Motion counts, regularity values, intensity values, and METs may indicate an amount of user motion (e.g., velocity/acceleration) over time. Orientation values may indicate how the ring 104 is oriented on the user's finger and if the ring 104 is worn on the left hand or right hand.

In some implementations, motion counts and regularity values may be determined by counting a number of acceleration peaks within one or more periods of time (e.g., one or more 30 second to 1 minute periods). Intensity values may indicate a number of movements and the associated intensity (e.g., acceleration values) of the movements. The intensity values may be categorized as low, medium, and high, depending on associated threshold acceleration values. METs may be determined based on the intensity of movements during a period of time (e.g., 30 seconds), the regularity/irregularity of the movements, and the number of movements associated with the different intensities.

In some implementations, the processing module 230-*a* may compress the data stored in memory 215. For example, the processing module 230-*a* may delete sampled data after making calculations based on the sampled data. As another example, the processing module 230-*a* may average data over longer periods of time in order to reduce the number of stored values. In a specific example, if average temperatures for a user over one minute are stored in memory 215, the processing module 230-*a* may calculate average temperatures over a five minute time period for storage, and then subsequently erase the one minute average temperature data. The processing module 230-*a* may compress data based on a variety of factors, such as the total amount of used/available memory 215 and/or an elapsed time since the ring 104 last transmitted the data to the user device 106.

Although a user's physiological parameters may be measured by sensors included on a ring 104, other devices may measure a user's physiological parameters. For example, although a user's temperature may be measured by a temperature sensor 240 included in a ring 104, other devices may measure a user's temperature. In some examples, other wearable devices (e.g., wrist devices) may include sensors that measure user physiological parameters. Additionally, medical devices, such as external medical devices (e.g., wearable medical devices) and/or implantable medical devices, may measure a user's physiological parameters. One or more sensors on any type of computing device may be used to implement the techniques described herein.

The physiological measurements may be taken continuously throughout the day and/or night. In some implementations, the physiological measurements may be taken during portions of the day and/or portions of the night. In some implementations, the physiological measurements may be taken in response to determining that the user is in a specific state, such as an active state, resting state, and/or a sleeping state. For example, the ring 104 can make physiological measurements in a resting/sleep state in order to acquire cleaner physiological signals. In one example, the ring 104 or other device/system may detect when a user is resting and/or sleeping and acquire physiological parameters (e.g., temperature) for that detected state. The devices/systems may use the resting/sleep physiological data and/or other data when the user is in other states in order to implement the techniques of the present disclosure.

In some implementations, as described previously herein, the ring 104 may be configured to collect, store, and/or process data, and may transfer any of the data described herein to the user device 106 for storage and/or processing. In some aspects, the user device 106 includes a wearable application 250, an operating system (OS), a web browser application (e.g., web browser 280), one or more additional applications, and a GUI 275. The user device 106 may further include other modules and components, including sensors, audio devices, haptic feedback devices, and the like. The wearable application 250 may include an example of an application (e.g., "app") that may be installed on the user device 106. The wearable application 250 may be configured to acquire data from the ring 104, store the acquired data, and process the acquired data as described herein. For example, the wearable application 250 may include a user interface (UI) module 255, an acquisition module 260, a processing module 230-*b*, a communication module 220-*b*, and a storage module (e.g., database 265) configured to store application data.

The various data processing operations described herein may be performed by the ring 104, the user device 106, the servers 110, or any combination thereof. For example, in some cases, data collected by the ring 104 may be pre-processed and transmitted to the user device 106. In this example, the user device 106 may perform some data processing operations on the received data, may transmit the data to the servers 110 for data processing, or both. For instance, in some cases, the user device 106 may perform processing operations that require relatively low processing power and/or operations that require a relatively low latency, whereas the user device 106 may transmit the data to the servers 110 for processing operations that require relatively high processing power and/or operations that may allow relatively higher latency.

In some aspects, the ring 104, user device 106, and server 110 of the system 200 may be configured to evaluate sleep patterns for a user. In particular, the respective components of the system 200 may be used to collect data from a user via the ring 104, and generate one or more scores (e.g., Sleep Score, Readiness Score) for the user based on the collected data. For example, as noted previously herein, the ring 104 of the system 200 may be worn by a user to collect data from the user, including temperature, heart rate, HRV, and the like. Data collected by the ring 104 may be used to determine when the user is asleep in order to evaluate the user's sleep for a given "sleep day." In some aspects, scores may be calculated for the user for each respective sleep day, such that a first sleep day is associated with a first set of scores, and a second sleep day is associated with a second set of scores. Scores may be calculated for each respective sleep day based on data collected by the ring 104 during the respective sleep day. Scores may include, but are not limited to, Sleep Scores, Readiness Scores, and the like.

In some cases, "sleep days" may align with the traditional calendar days, such that a given sleep day runs from midnight to midnight of the respective calendar day. In other cases, sleep days may be offset relative to calendar days. For example, sleep days may run from 6:00 pm (18:00) of a calendar day until 6:00 pm (18:00) of the subsequent calendar day. In this example, 6:00 pm may serve as a "cut-off time," where data collected from the user before 6:00 pm is counted for the current sleep day, and data collected from the user after 6:00 pm is counted for the subsequent sleep day. Due to the fact that most individuals sleep the most at night, offsetting sleep days relative to calendar days may enable the system 200 to evaluate sleep patterns for users in such a manner that is consistent with their sleep schedules. In some cases, users may be able to selectively adjust (e.g., via the GUI) a timing of sleep days relative to calendar days so that the sleep days are aligned with the duration of time that the respective users typically sleep.

In some implementations, each overall score for a user for each respective day (e.g., Sleep Score, Readiness Score) may be determined/calculated based on one or more "contributors," "factors," or "contributing factors." For example, a user's overall Sleep Score may be calculated based on a set of contributors, including: total sleep, efficiency, restfulness, REM sleep, deep sleep, latency, timing, or any combination thereof. The Sleep Score may include any quantity of contributors. The "total sleep" contributor may refer to the sum of all sleep periods of the sleep day. The "efficiency" contributor may reflect the percentage of time spent asleep compared to time spent awake while in bed, and may be calculated using the efficiency average of long sleep periods (e.g., primary sleep period) of the sleep day, weighted by a duration of each sleep period. The "restfulness" contributor may indicate how restful the user's sleep is, and may be calculated using the average of all sleep periods of the sleep day, weighted by a duration of each period. The restfulness contributor may be based on a "wake up count" (e.g., sum of all the wake-ups (when user wakes up) detected during different sleep periods), excessive movement, and a "got up count" (e.g., sum of all the got-ups (when user gets out of bed) detected during the different sleep periods).

The "REM sleep" contributor may refer to a sum total of REM sleep durations across all sleep periods of the sleep day including REM sleep. Similarly, the "deep sleep" contributor may refer to a sum total of deep sleep durations across all sleep periods of the sleep day including deep sleep. The "latency" contributor may signify how long (e.g., average, median, longest) the user takes to go to sleep, and may be calculated using the average of long sleep periods throughout the sleep day, weighted by a duration of each period and the number of such periods (e.g., consolidation of a given sleep stage or sleep stages may be its own contributor or weight other contributors). Lastly, the "timing" contributor may refer to a relative timing of sleep periods within the sleep day and/or calendar day, and may be calculated using the average of all sleep periods of the sleep day, weighted by a duration of each period.

By way of another example, a user's overall Readiness Score may be calculated based on a set of contributors, including: sleep, sleep balance, heart rate, HRV balance, recovery index, temperature, activity, activity balance, or any combination thereof. The Readiness Score may include any quantity of contributors. The "sleep" contributor may refer to the combined Sleep Score of all sleep periods within the sleep day. The "sleep balance" contributor may refer to a cumulative duration of all sleep periods within the sleep day. In particular, sleep balance may indicate to a user whether the sleep that the user has been getting over some duration of time (e.g., the past two weeks) is in balance with the user's needs. Typically, adults need 7-9 hours of sleep a night to stay healthy, alert, and to perform at their best both mentally and physically. However, it is normal to have an occasional night of bad sleep, so the sleep balance contributor takes into account long-term sleep patterns to determine whether each user's sleep needs are being met. The "resting heart rate" contributor may indicate a lowest heart rate from the longest sleep period of the sleep day (e.g., primary sleep period) and/or the lowest heart rate from naps occurring after the primary sleep period.

Continuing with reference to the "contributors" (e.g., factors, contributing factors) of the Readiness Score, the "HRV balance" contributor may indicate a highest HRV average from the primary sleep period and the naps happening after the primary sleep period. The HRV balance contributor may help users keep track of their recovery status by comparing their HRV trend over a first time period (e.g., two weeks) to an average HRV over some second, longer time period (e.g., three months). The "recovery index" contributor may be calculated based on the longest sleep period. Recovery index measures how long it takes for a user's resting heart rate to stabilize during the night. A sign of a very good recovery is that the user's resting heart rate stabilizes during the first half of the night, at least six hours before the user wakes up, leaving the body time to recover for the next day. The "body temperature" contributor may be calculated based on the longest sleep period (e.g., primary sleep period) or based on a nap happening after the longest sleep period if the user's highest temperature during the nap is at least 0.5° C. higher than the highest temperature during the longest period. In some aspects, the ring may measure a user's body temperature while the user is asleep, and the system 200 may display the user's average temperature relative to the user's baseline temperature. If a user's body temperature is outside of their normal range (e.g., clearly above or below 0.0), the body temperature contributor may be highlighted (e.g., go to a "Pay attention" state) or otherwise generate an alert for the user.

In some aspects, the system 200 may support a wearable device 104 that includes a battery in the cover of the wearable device 104. In particular, techniques described herein support a ring 104, such as a wearable device 104 as described with reference to FIG. 1. For example, a ring 104 may include an inner housing 205-a and an outer housing 205-b configured to house one or more sensors and configured to acquire physiological data from a user 102. The outer housing 205-b may be an example of the outer cover or "outer shell component" described herein. The one or more sensors of the ring 104 may obtain physiological measurements from the user 102 (e.g., temperature sensors, additional LED-PD sensors used for measuring heart rate, oxygen saturation, one or more sensors that a device may use to detect whether a user is asleep, or the like).

In some cases, the one or more sensors of the ring 104 are configured to acquire the physiological data from the user 102 based on arterial blood flow, temperature, etc. In some implementations, the one or more sensors of the ring 104 are configured to acquire the physiological data (e.g., including PPG data) from the user 102 based on blood flow that is diffused into the microvascular bed of skin with capillaries and arterioles. The one or more sensors of the ring 104 may be an example of photodetectors from the PPG system 235, temperature sensors 240, motion sensors 245, and other sensors.

As described herein, the wearable device of the system 200 may include a battery that is positioned between the inner housing 205-a and the outer housing 205-b. Positioning the battery within the cover (e.g., between the inner housing 205-a and the outer housing 205-b, positioning the battery at least partially into the outer housing 205-b) of the wearable device 104 may enable the wearable device 104 to support additional functions based on the reduced thickness of the battery and overlapping the battery with the one or more sensor of the ring 104. By using the cover as a wall of a battery chamber configured to enclose the battery, a thickness of the battery may be further reduced, thereby alleviating spatial and structural constraints on the placement of the one or more sensors around the ring 104.

While much of the present disclosure describes one or more components in the context of a wearable ring device 104, aspects of the present disclosure may additionally or alternatively be implemented in the context of other wearable devices 104. For example, in some implementations, the one or more components described herein may be implemented in the context of other wearable devices, such as bracelets, watches, other wrist-worn wearables, necklaces, piercings, and the like. For example, the wearable device 104 may surround a finger, wrist, ankle, earlobe, or the like of a user.

For example, as noted previously herein, the ring 104 of the system 200 may be worn by a user 102 to collect data from the user 102, including temperature data, sleep data, recovery data, activity data, heart rate data, HRV data, respiratory data, breathing rate data, blood pressure data, blood glucose data, and the like. The ring 104 of the system 200 may collect the physiological data from the user 102 based on temperature sensors and measurements extracted from arterial blood flow (e.g., using PPG signals). In some cases, the ring 104 may collect the physiological data from the user 102 based on measurements extracted from capillary blood flow, arteriole blood flow, or both.

In some implementations, the one or more sensors of the ring 104 may sample the user's temperature continuously throughout the day and night. Sampling at a sufficient rate (e.g., one sample per minute) throughout the day and/or night may provide sufficient temperature data for analysis described herein. In some implementations, the ring 104 may continuously acquire temperature data (e.g., at a sampling rate). In some examples, even though temperature data is collected continuously, the system 200 may leverage other information about the user 102 that it has collected or otherwise derived (e.g., sleep stage, activity levels, illness onset, etc.) to select a representative temperature for a particular day that is an accurate representation of the underlying physiological phenomenon.

Figure 3:
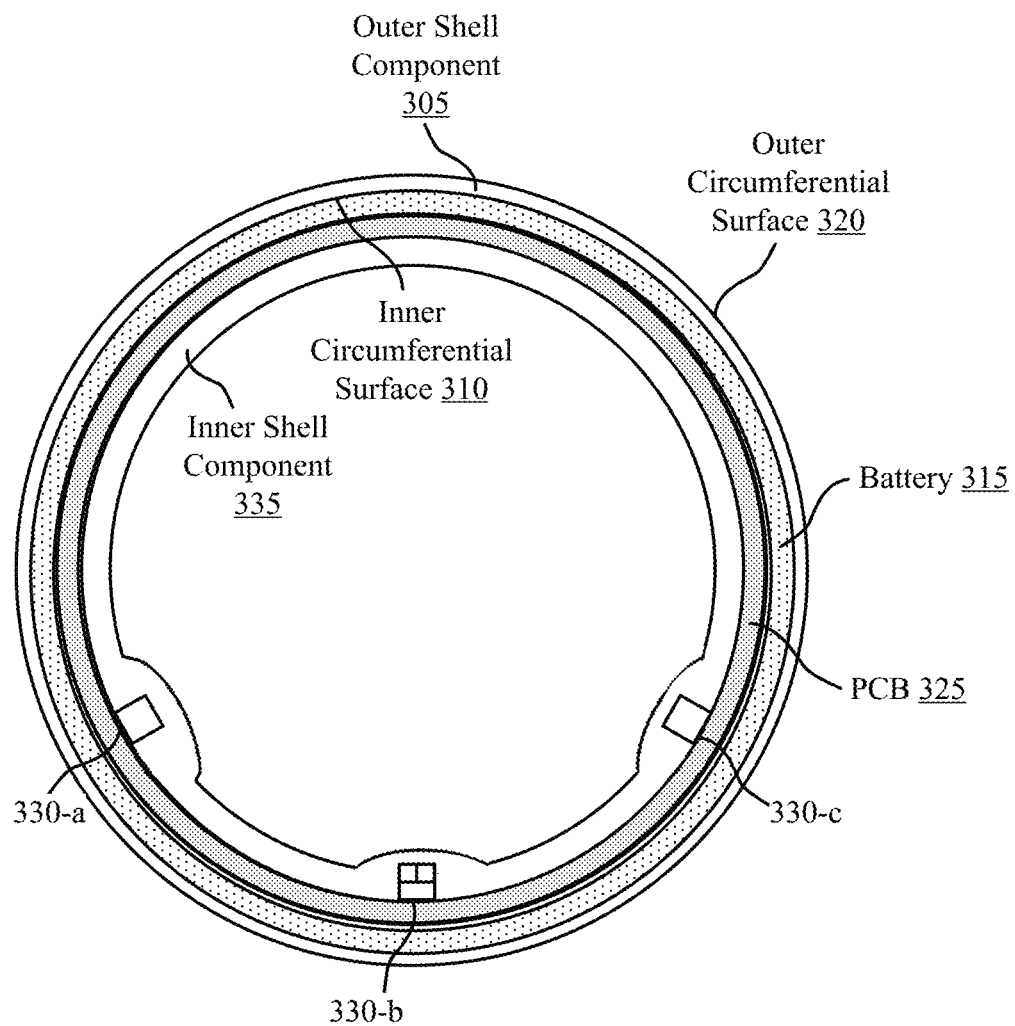
FIG. 3 shows an example of a wearable ring device that supports a wearable ring device with a battery in the cover of the device in accordance with aspects of the present disclosure.

FIG. 3 shows an example of a wearable ring device 300 that supports a wearable ring device with a battery in the cover of the device in accordance with aspects of the present disclosure. The wearable ring device 300 may implement, or be implemented by, aspects of the system 100, system 200, or both. For example, the wearable ring device 300 may illustrate an example of a wearable device 104 as described with reference to FIG. 1. Although the wearable ring device 300 is illustrated as a ring in FIG. 3, the wearable ring device 300 may be any example of a wearable device (e.g., a wrist-worn wearable, a necklace, and the like).

The wearable ring device 300 may include a circumferential housing that includes an inner shell component 335 and an outer shell component 305, which may be examples of an inner housing 205-a and an outer housing 205-b, respectively, as described with reference to FIG. 2. The outer shell component 305 may be an example of a ring outer cover. The outer shell component 305 may include an outer circumferential surface 320 and an inner circumferential surface 310 opposite the outer circumferential surface 320.

The wearable ring device 300 may include a battery 315, a PCB 325, and sensors 330. In some wearable devices, the location of the battery 315 with respect to the PCB 325 may prevent placing the PCB 325 or components of the PCB 325 in areas that are overlapping with the battery 315. For example, in some wearable ring devices, the battery 315 may take up almost the entire width of the wearable ring device 300, and span approximately 140° around the full circumference of the wearable ring device 300. In such cases, due to the thickness of the battery 315, sensors 330 may not be placed on top of (e.g., overlap with) the battery 315, as doing so would make the wearable ring device too thick and uncomfortable to wear. In such cases, because sensors 330 cannot be placed on top of the battery 315 in some wearable ring devices due to the thickness of the battery 315, the position of other sensors 330 may be restricted to the remaining 220° around the circumference of the wearable ring device 300 that is not occupied by the battery 315.

In addition, in some wearable ring devices, the size of the battery 315 may be the main limiting factor for the overall size of the wearable ring device 300. For example, increasing a capacity of the battery 315 may further increase a size of the battery 315 and thereby increasing a size of the wearable ring device 300. The thickness of the battery 315 may be made of multiple anode/cathode layers and walls of battery housing that contains the anode/cathode layers. Accordingly, to reduce an overall thickness of the wearable ring device 300 and improve the performance of the battery 315, the sensors 330, or both, aspects of the present disclosure are directed to wearable ring devices 300 with a battery 315 in the cover (e.g., the outer shell component 305) of the wearable ring device 300.

The battery 315 may extend radially around at least a portion of a circumference of the wearable ring device 300. In some examples, the battery 315 may extend radially around a full circumference (e.g., an entire portion) of the wearable ring device 300. In such cases, the battery 315 may extend 360° around the wearable ring device 300. In additional or alternative cases, the battery 315 may span radially around less than the full circumference of the wearable ring device (e.g., battery may span 180°, 270°, etc.).

In some aspects, the battery 315 may have both flexible and rigid sections such that the battery 315 may radially extend around the circumference of the wearable ring device 300. In some cases, the battery 315 may include flexible sections that extend around the entire circumference of the wearable ring device 300. Additionally, or alternatively, the battery 315 may be made up of multiple battery segments that are electrically coupled to one another via flexible sections (e.g., wires, etc.). By extending the battery 315 around a portion of the circumference (or around an entire circumference) of the wearable ring device 300, an overall thickness of the battery 315 may be reduced, thereby allowing other components or circuitry (e.g., sensors 330) to be embedded throughout and around the wearable ring device 300.

In some cases, the battery 315 may include a set of anode and cathode layers. The quantity of anode and cathode layers of the wearable ring device 300 may be less than the quantity of anode and cathode layers of previous wearable ring devices, thereby reducing the overall thickness of the battery 315. Moreover, according to aspects of the present disclosure, the capacity of the battery 315 may be increased without increasing the overall thickness of the wearable ring device 300 such as, for example, increasing how far the battery 315 extends radially around the circumference of the wearable ring device. In other words, using techniques described herein, the capacity of the battery 315 may be increased by: (1) adding additional anode/cathode layers, and/or (2) increasing the surface area and/or radial span of the battery 315.

While much of the present disclosure illustrates the battery 315 extending around the entire circumference of the wearable ring device 300, aspects of the present disclosure may additionally or alternatively implement a battery 315 that spans any angular range of the wearable ring device 300. For example, in some implementations, the battery 315 may span 20° around the circumference of the wearable ring device 300, 180° around the circumference of the wearable ring device 300, 300° around the circumference of the wearable ring device 300, and the like.

In some examples, the battery 315 may be a rechargeable battery, which may be an example of the battery 210 as described with reference to FIG. 2. For example, the battery 315 may include a Lithium-Ion or Lithium-Polymer type battery, although a variety of battery options are possible. In some aspects, the outer shell component 305 may also include a charging component that may be used to charge the battery 315 when electrically coupled to the battery 315. That is, the charging component may be configured to receive an electrical current from a power source to charge the battery 315 when the charging component is electrically coupled to the battery 315. The battery 315 may be wirelessly charged (e.g., via inductive charging components, electronic contact components, etc.), charged via a wired connection to a power source, or a combination thereof. In some cases, the battery 315 may be rechargeable while attached with the wearable ring device 300.

The wearable ring device 300 may include an electronic substrate, such as a printed wiring board (PWB) or PCB 325. The PCB 325 may have both flexible and rigid sections. In some cases, the PCB 325 may include flexible sections that extend around an entire circumference of the ring. Electrical components may be embedded in the PCB 325 of the wearable ring device 300. The electrical components of the wearable ring device 300 may include one or more sensors 330 (e.g., temperature sensors, light sources, photodetectors) configured to acquire physiological data associated with the user. The one or more sensors 330 of the wearable ring device 300 may be positioned at least partially within the circumferential housing of the wearable ring device 300.

The sensors 330 may be configured to acquire physiological data associated with the user. In some examples, the sensors 330 may be positioned at least partially within the circumferential housing (e.g., between the inner shell component 335 and the outer shell component 305). For example, the wearable ring device 300 may include a sensor 330-a, a sensor 330-b, and a sensor 335-c, where the sensors 330 may be embedded within the inner shell component 335. The sensors 330 may be electrically coupled with the battery 315 (e.g., via contacts between the PCB 325 and the battery 315, as will be described in further detail herein).

In some cases, the sensors 330 including light-emitting components and photodetectors may be disposed on the PCB 325 at a location within the portion of the circumference of the wearable ring device 300 where the PCB 325 overlaps with the battery 315. In other words, aspects of the present disclosure may enable the battery 315 to be thinner, thereby enabling sensors 330 (e.g., light-emitting components, photodetectors, etc.) to be placed on top of (e.g., overlap with) the battery 315. In such cases, one or more sensors 330 may overlap the battery 315 for a portion of the circumference of the wearable ring device 300. The sensors 330 may be positioned radially around at least the same portion of the circumference of the wearable ring device 300 that the battery 315 extends around. In some examples, the sensors 330 may be positioned radially around a full circumference (e.g., an entire portion) of the wearable ring device 300.

By integrating a thinner battery 315 into and around the wearable ring device 300, the sensors 330 may be placed around various overlapping locations of the wearable ring device 300 (and in locations that do not overlap with the battery 315) rather than being confined to a defined portion opposite or adjacent to the battery 315. In some cases, the quantity and quality of the signals measured by the sensors 330 may be improved by placing the sensors 330 on top (e.g., in overlapping portions) of the battery 315. Specifically, enabling sensors 330 to be placed around the full circumference of the ring may increase how many optical channels (LED-photodetector channels) that are available for performing physiological measurements, thereby making the ring more robust to conditions that may otherwise limit the ability of the ring to collect data, such as the ring becoming rotated, certain optical channels becoming blocked, etc. Further, in some examples, the performance and charging capacity of the battery 315 may be improved by extending the battery 315 around the circumference of the wearable ring device 300.

Figure 4:
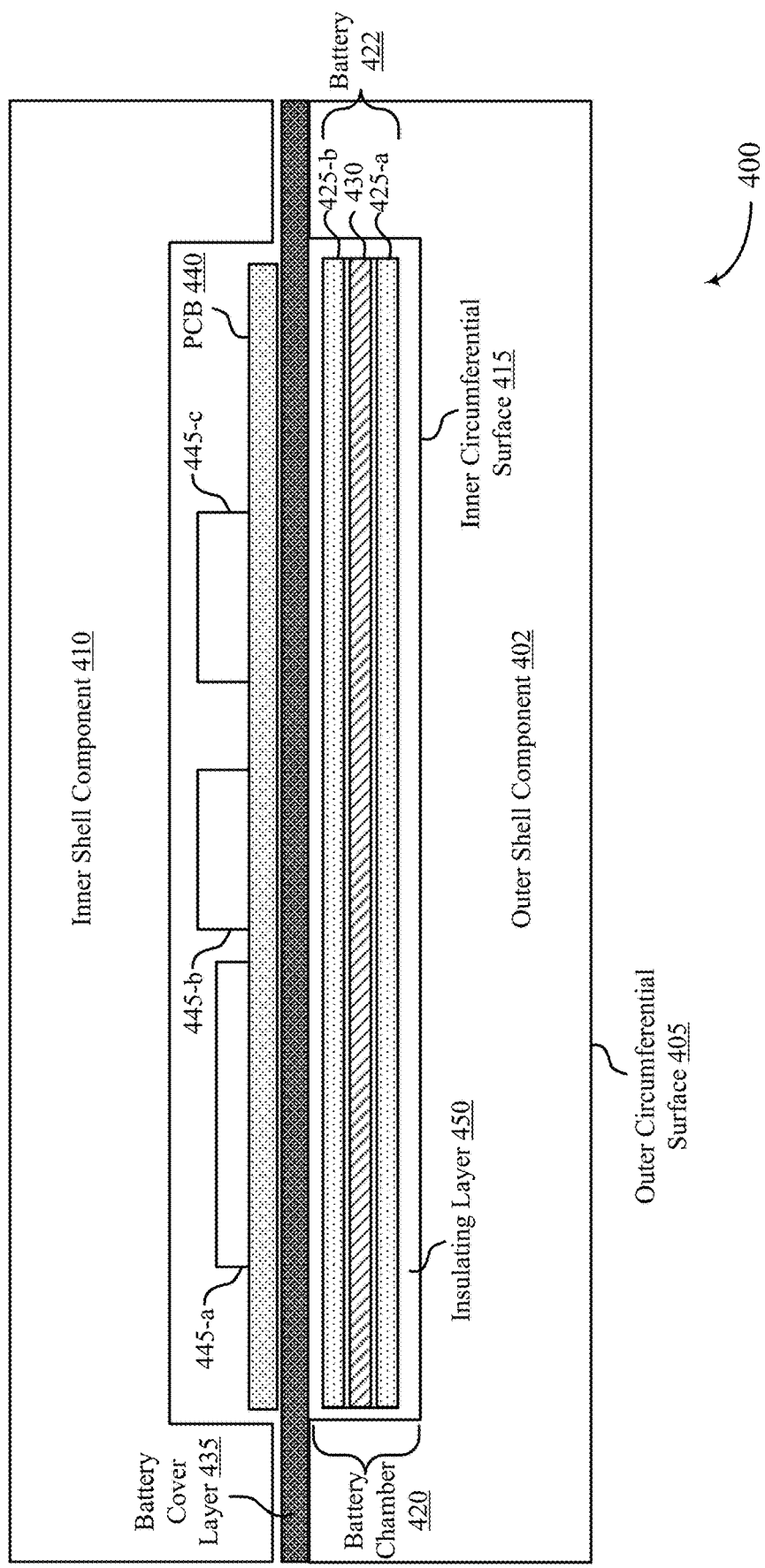
FIG. 4 shows an example of a wearable ring device diagram that supports a wearable ring device with a battery in the cover of the device in accordance with aspects of the present disclosure.

FIG. 4 shows an example of a wearable ring device diagram 400 that supports a wearable ring device with a battery in the cover of the device in accordance with aspects of the present disclosure. The wearable ring device diagram 400 may implement, or be implemented by, aspects of the system 100, system 200, wearable ring device 300, or any combination thereof. For example, the wearable ring device diagram 400 may illustrate an example of the wearable ring device 300 as described with reference to FIG. 3. In such cases, the wearable ring device diagram 400 may illustrate a side cross-sectional view of a portion of the wearable ring device 300 as described with reference to FIG. 3.

The wearable ring device diagram 400 may include an outer shell component 402 and an inner shell component 410. The outer shell component 402 may include an inner circumferential surface 415 and an outer circumferential surface 405 opposite the inner circumferential surface 415. The wearable ring device diagram 400 may include a battery cover layer 435. The battery cover layer 435 may be coupled with portions of the inner circumferential surface 415 of the outer shell component 402. For example, the inner circumferential surface 415 may extend parallel along a surface of the battery cover layer 435. In some cases, the inner circumferential surface 415 extend perpendicular towards a surface of the outer circumferential surface 405, extend parallel to the surface of the outer circumferential surface 402, and extend perpendicular away from the surface of the outer circumferential surface 405 to form a cavity in the outer shell component 402. In other cases, the inner circumferential surface 415 may be curved to create the cavity in the outer shell component 402. The cavity may be an example of a battery chamber 420 configured to house the battery 422. In this regard, the battery 422 may be built into the outer shell component 402 such that the inner circumferential surface 415 of the outer shell component 402 forms one or more structural boundaries of the battery chamber 420 that houses the battery 422.

Structural boundaries of the battery chamber 420 may be formed by the cavity within the outer shell component 402. For example, the structural boundaries of the battery chamber 420 may include at least three sides of the inner circumferential surface 415 and one side of the battery cover layer 435. The battery chamber 420 may form a liquid-tight enclosure by coupling the battery cover layer 435 to the inner circumferential surface 415. In some cases, the battery cover layer 435 may be an example of an aluminum film. For example, the battery cover layer 435 may be an example of the aluminum film to create an aluminum pouch that encloses the battery 422 within the outer shell component 402. In such cases, the outer shell component 402 may protect the battery 422, thereby using the ring cover as a shielding structure for components of the battery 422.

Some previous wearable ring devices may include a separate aluminum pouch configured to enclose the battery 422. In other words, previous wearable devices may include a dedicated aluminum pouch that completely surrounds the battery 422 on all sides to form the battery chamber 420. In such cases, previous wearable ring devices may include an additional aluminum layer (e.g., an additional aluminum cover layer 425) between the battery 422 and the outer shell component 402, thereby increasing the total thickness of the battery 422.

To reduce the overall thickness of the ring and improve manufacturing costs, wearable ring device diagram 400 may form the aluminum pouch within the outer shell component 402 by using an inner circumferential surface 415 of the outer shell component 402 as one of the sides of the battery chamber 420. In other words, aspects of the present disclosure may re-purpose the inner circumferential surface 415 of the outer shell component 402 as a structural boundary of the battery chamber 420 to reduce the overall thickness of the battery 422. In such cases, the battery cover layer 435 and the inner circumferential surface 415 of the outer shell component 402 may form the cavity (e.g., the aluminum pouch) of the battery chamber 420. For example, the inner circumferential surface 415 of the outer shell component 402 may be used as structural boundaries of the liquid-tight battery chamber 420. In some cases, the cavity of the battery chamber 420 may include a flexible cavity. That is, one or more structural boundaries of the battery chamber 420 (such as the battery cover layer 435) may be flexible to allow the cavity of the battery chamber 420 to expand and contract. For example, as the anode layers 425 and the cathode layers 430 swell and/or change size based on the state of the charge of the battery 422, the cavity may be flexible to accommodate the swelling of the battery 422.

The battery chamber 420 may be configured to enclose a set of anode layers 425 and a cathode layer 430 of the battery 422. The battery 422 may include two anode layers 425 and one cathode layer 430. For example, the battery 422 may include a first anode layer 425-a, a cathode layer 430, and a second anode layer 425-b. In such cases, the cathode layer 430 may be positioned between the first anode layer 425-a and the second anode layer 425-b. The first cathode layer 430 may be disposed on top of the first anode layer 425-a, and the second anode layer 425-b may be disposed on top of the cathode layer 430. In some cases, each anode layer 425 and cathode layer 430 may include a same thickness. The anode layers 425 and cathode layer 430 may each extend a same length. In such cases, the anode layers 425 may align with the cathode layer 430.

Some previous wearable ring devices may include nine to twelves layers of anode layers 425 and cathode layers 430. However, the wearable ring device diagram 400 may include three layers that may decrease the overall thickness of the battery 422 and the wearable ring device. The area of the battery 422 may be increased by increasing the length of the battery layers (e.g., the anode layers 425 and the cathode layer 430) to extend around a portion of the circumference of the wearable ring device.

Swelling effects caused by temperature variations of the battery 422 may be reduced based on decreasing a quantity of battery layers within the battery chamber 420. In some cases, the swelling effects of the battery 422 may be caused by charging and discharging the battery 422. The anode layers 425 and the cathode layer 430 may increase or decrease in thickness as the charge of the battery 422 changes. In such cases, a reduction in a quantity of anode layers 425 and cathode layers 430 (according to techniques described herein) may reduce the swelling effects of the battery 422.

In some examples, including three total layers of anode layers 425 and cathode layers 430 may reduce a quantity of layers and reduce an area for gasses to form, thereby reducing the overall swelling of the battery 422. The gasses may be formed from the charge carriers (e.g., electrolyte fluid) within the battery chamber 420. By decreasing the thickness of the battery 422 (e.g., by reducing the quantity of anode/cathode layers), the volume of the battery 422 may decrease, thereby reducing the amount of electrolyte fluid within the battery chamber 420. In this regard, by reducing the amount of electrolyte fluid, the amount of gasses formed during the lifetime of the battery 422 may also be reduced.

While much of the present disclosure shows and describes two anode layers 425 and one cathode layer 430, aspects of the present disclosure may additionally or alternatively implement any quantity of anode layers 425 cathode layers 430 in the battery 422. The battery 422 may include one more anode layer 430 than cathode layers 430. For example, the battery 422 may include three anode layers 425 and two cathode layers 430.

In some cases, separator layers may be disposed between the anode layers 425 and the cathode layer 430. For example, a first separator layer may be positioned between the cathode layer 430 and the first anode layer 425-*a*, and a second separator layer may be positioned between the cathode layer 430 and the second anode layer 425-*b*. In such cases, the cathode layer 430 may be disposed on top of the first separator layer, and the second anode layer 425-*b* may be disposed on top of the second separator layer. In some aspects, the separator layers may be perforated to enable charge carriers (e.g., an electrolyte fluid) to flow across the separator layers and between the respective anode/cathode layers. Charge carriers, such as an electrolyte fluid, may be an example of particles or holes that may freely move within a material and carry an electric charge.

In some aspects, the battery chamber 420 may include an insulating layer 450. The insulating layer 450 may be configured to outline the one or more structural boundaries of the battery chamber 420 and enclose the set of anode layers 425 and the cathode layer 430 of the battery 422 within the battery chamber 420. For example, the insulating layer 450 may be coupled to (e.g., disposed on) the inner circumferential surface 415 of the outer shell component 402 and the battery cover layer 435. In such cases, the insulating layer 450 may be coupled with three sides of the inner circumferential surface 415 and one side of the battery cover layer 435. In some cases, the insulating layer 450 may be included when the outer shell component 402 includes a titanium material, a conductive material, or both. The insulating layer 450 may be an example of a soft, flexible material or coating configured to reduce the effects of swelling caused by temperature variations of the battery 422. Moreover, the insulating layer 450 or coating may be configured to protect the battery cover layer 435 and/or outer shell component 402 from corrosion caused by charge carriers (e.g., electrolyte fluid) within the battery chamber 420. In some cases, the insulating layer 450 may reduce the pressure on the electronics disposed on the PCB 440, the battery 422, the one or more sensors 445, or any combination thereof.

The insulating layer 450 may be disposed around the battery 422. In such cases, the insulating layer 450 forms a liquid-tight enclosure by enclosing the set of anode layers 425 and the cathode layer 430 within the battery chamber 420. For example, the first anode layer 425-*a* may be positioned between the insulating layer 450 and the cathode layer 430, the first separator layer, or both. In such cases, the first anode layer 425-*a* may be on top of the insulating layer 450. The second anode layer 425-*b* may be positioned between the insulating layer 450 and the cathode layer 430, the second separator layer, or both. In such cases, the insulating layer 450 may be on top of the second anode layer 430-*b*. For example, the insulating layer 450 may be positioned between the second anode layer 425-*b* and the battery cover layer 435.

In some cases, the battery chamber 420 may be configured to enclose charge carriers (e.g., electrolyte fluid). The separator layers between the anode layers 425 and the cathode layer 430 may include one or more holes (e.g., perforations) within the separator layer. In such cases, the charge carriers (e.g., electrolyte fluid) may flow between the anode layers 425 and the cathode layer 430 through the holes of the separator layers. In some cases, the charge carriers may contact at least a portion of the insulating layer 450 disposed around the battery 422. In additional or alternative examples, such as in cases without an insulating layer 450, the charge carriers (e.g., electrolyte fluid) may contact at least a portion of the inner circumferential surface 415 of the outer shell component 402 within the battery chamber 420. In such cases, the insulating layer 450 may be absent from one or more portions within the battery chamber 420, and the charge carriers (e.g., electrolyte fluid) may contact at least a portion of the inner circumferential surface 415, the battery cover layer 435, or both. The insulating layer 450 may be absent when the outer shell component 402 includes an insulating material, or when the outer shell component 402 is otherwise resistant to corrosion from the charge carriers.

The wearable device diagram 400 may include a PCB 440. The PCB 440 may be positioned on a portion of the battery cover layer 435. For example, the PCB 440 may be coupled with the battery cover layer 435 and extend along a portion of the battery cover layer 435. In such cases, the PCB 440 may overlap with the battery 422 for at least a portion of the circumference of the wearable ring device.

The PCB 440 may include a plurality of sensors 445-*a*, 445-*b*, 445-*c*. The sensors 445 may be configured to acquire physiological data and may be electrically coupled to the battery 422. For example, the sensors 445 may include light-emitting components (e.g., LEDs), photodetectors, temperature sensors, electrodes, and the like. In some cases, the sensors 445 may be positioned on a surface of the PCB 440 opposite of the battery chamber 420. For example, the sensors 445 may extend away from a surface of the PCB 440 and towards the inner shell component 410. The sensors 445 may be positioned to extend away from the battery 422 to mitigate temperature effects that the battery 422 may have on the sensors 445.

Figure 5:
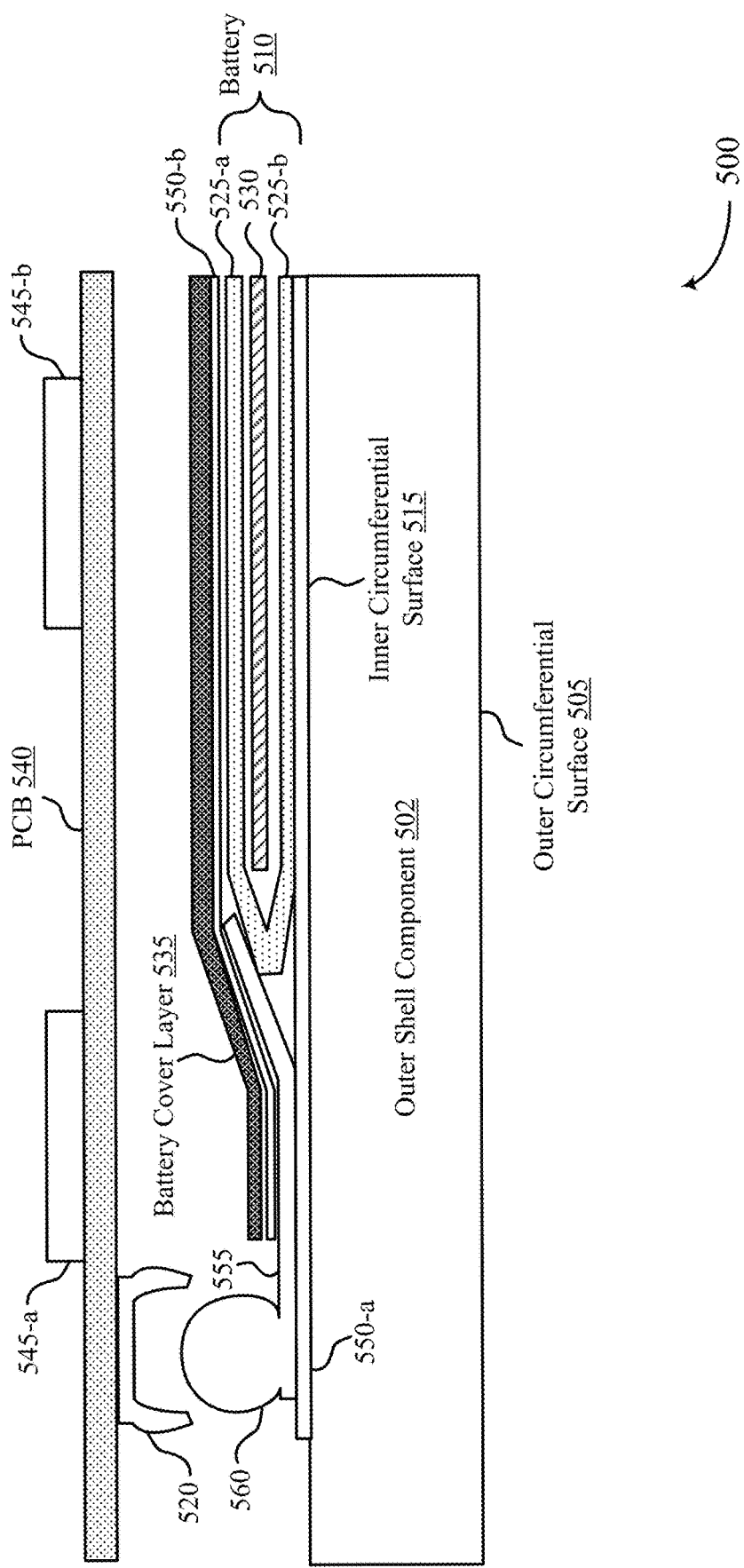
FIG. 5 shows an example of a wearable ring device diagram that supports a wearable ring device with a battery in the cover of the device in accordance with aspects of the present disclosure.

FIG. 5 shows an example of a wearable device diagram 500 that supports a wearable ring device with a battery in the cover of the device in accordance with aspects of the present disclosure. The wearable ring device diagram 500 may implement, or be implemented by, aspects of the system 100, system 200, wearable ring device 300, wearable ring device diagram 400, or any combination thereof. For example, the wearable ring device diagram 500 may illustrate an example of the wearable ring device 300 as described with reference to FIG. 3. In such cases, the wearable ring device diagram 500 may illustrate a side view of a portion of the wearable ring device 300 as described with reference to FIG. 3.

The wearable ring device diagram 500 may include an outer shell component 502. The outer shell component 502 may be an example of the outer shell component 402 as described with reference to FIG. 4. For example, the outer shell component 502 may include an inner circumferential surface 515 and an outer circumferential surface 505 opposite the inner circumferential surface 515. An insulating layer 550-*a* may be positioned on the inner circumferential surface 515 and coupled with the battery 510. The insulating layer 550 and the battery 510 may be examples of the insulating layer 450 and the battery 422, respectively, as described with reference to FIG. 4. For example, the battery 510 may include a first anode layer 525-*a*, a cathode layer 530, and a second anode layer 525-*b*. The insulating layer 550-*b* may be positioned between the second anode layer 525-*b* and the battery cover layer 535. The battery cover layer 535 may be an example of the battery cover layer 435 as described with reference to FIG. 4.

The wearable ring device diagram 500 may include one or more battery tabs 555, a connection element 560, and a contact element 520. While the wearable ring device diagram 500 illustrates a single battery tab 555, connection element 560, and contact element 520, the wearable ring device diagram 500 may additionally include a second battery tab 555, a second connection element 560, and a second contact element 520. For example, the wearable ring device diagram 500 may include a first battery tab 555 electrically coupled to the anode layers 525 and a second battery tab 555 electrically coupled to the cathode layer 530. The first battery tab 555 and the second battery tab 555 may form a negative and positive battery terminal for the electronics, respectively. The battery tabs 555 may be electrically coupled to the respective anode/cathode layers using one or more electrically conductive methods or materials. For example, in some cases, a welding procedure may connect the battery tabs 555 to the anode/cathode layers of the battery 510.

The battery tabs 555 may electrically couple the set of anode layers 525 and the cathode layer 530 to the PCB 540. For example, the battery tabs 555 may extend from within the battery chamber such that the first battery tab 555 is positioned between the insulating layer 550-*b* and the second anode layer 525-*b*. A second battery tab 555 may be coupled to the cathode layer 530. As the battery tabs 555 extends from within the battery chamber, the battery tab 555 may be positioned between the insulating layer 550-*a* and the insulating layer 550-*b* along a portion of the inner circumferential surface 515.

The battery tabs 555 may each be coupled with a connection element 560. The connection element 560 may be configured to electrically connect the battery tab 555 to the contact element 520. The contact element 520 may be disposed on a surface of the PCB 540. The contact element 520 may be an example of a metal contact of the PCB 540. In such cases, the connection element 560 and the contact element 520 may electrically couple the sensors 545 to the battery 510.

For example, the connection element 560 may be sized to fit within (or otherwise electrically couple with) the contact element 520 and directly contact the contact element 520 such that electrical current may flow from the battery 510 to the battery tab 555, to the connection element 560, and to the contact element 520. Because the contact element 520 directly contacts the PCB 540, the current may be transferred to the PCB 540 and to the sensors 545 to power the sensors 545 to perform measurements. The sensors 545-*a* and 545-*b* may be an example of a light-emitting source or a photodetector.

In some cases, the wearable ring device may include more than one battery 510 around the circumference of the wearable ring device. In such cases, each battery 510 may include corresponding battery tabs 555, connection elements 560, and contact elements 520. Moreover, in such cases, the PCB 540 may be electrically coupled to multiple batteries 510 dispersed around the circumference of the wearable device (and/or the wearable device may include separate PCBs 540 with corresponding batteries 510). The performance of the battery 510 and the sensors 545 may be improved as a quantity of batteries 510 and connection points (e.g., including the battery tabs 555, the connection elements 560, and the contact elements 520) increases. For each discrete battery 510, battery tabs 555 may be coupled to the battery 510. In some cases, each battery 510 may include a charging component. The charging component may be positioned on the PCB 540. In some cases, more than one battery 510 may be connected in series such that a single charging component may be coupled with more than one battery 510. In such cases, a single PCB 540 may be electrically coupled with multiple batteries 510.

In some cases, rather than having the battery tabs 555 extend from an end of the battery 510, the battery tabs 555 may extend from a side of the battery 510 in the case where the battery 510 extends around the entire circumference of the wearable ring device. In some cases, the battery tabs 555 may extend from the side of the battery 510 at multiple points along the inner circumferential surface 515, thereby connecting the battery 510 to the PCB 540 along multiple points of the PCB 540. In such cases, performance of the battery 510 and sensors 5454 may be improved by increasing a quantity of connection points and bringing the sensors 545 closer to the battery tabs 555. For example, a distance between the sensors 545 and the battery 510 may be reduced. In some cases, the performance of the battery 510 may increase by reducing a series resistance and allowing increased current flow through the battery 510.

Figure 6:
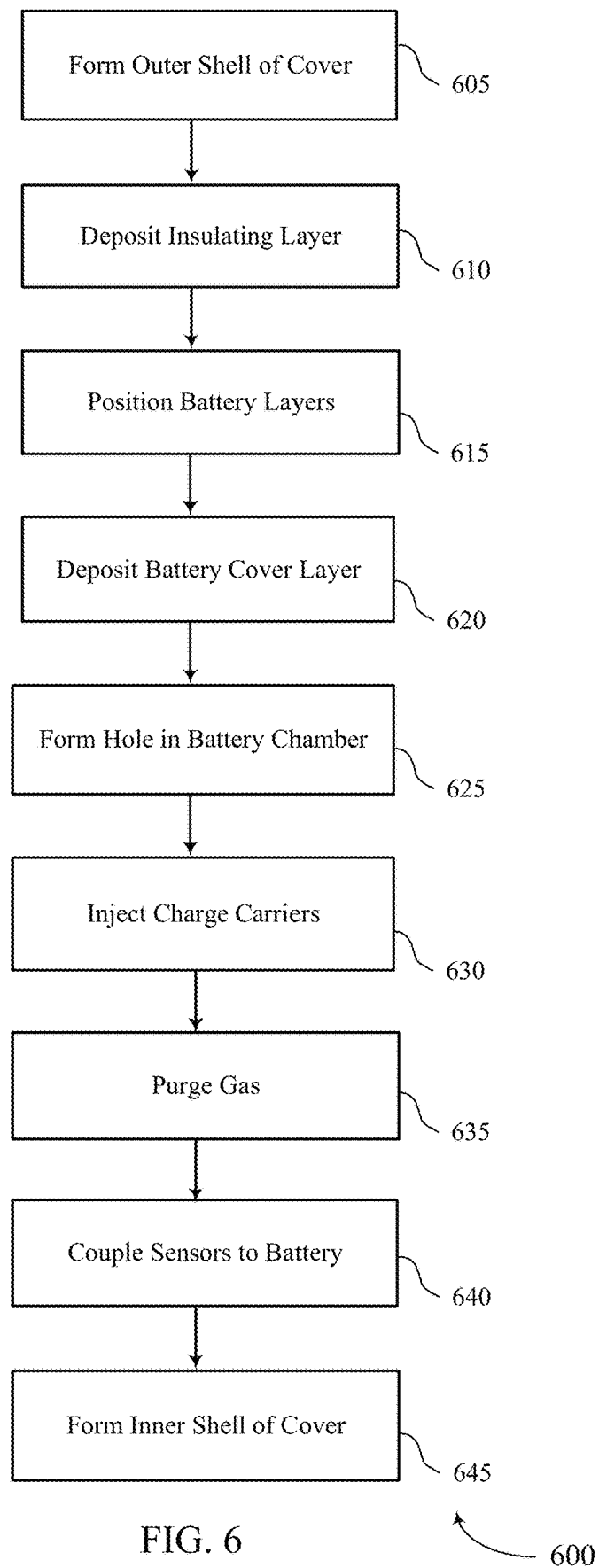
FIG. 6 shows an example of a process flow that supports a wearable ring device with a battery in the cover of the device in accordance with aspects of the present disclosure.

FIG. 6 shows an example of a process flow 600 that supports a wearable ring device with a battery in the cover of the device in accordance with aspects of the present disclosure. The operations of process flow 600 may be implemented by a system or its components as described herein. Alternative examples of the following may be implemented, where some steps are performed in a different order or not at all. Some steps may additionally include additional features not mentioned below. The process flow 600 illustrates techniques for manufacturing a wearable ring device to include a battery that extends radially around at least a portion of the circumference.

Aspects of the process flow 600 may be implemented by a controller, among other components. Additionally or alternatively, aspects of the process flow 600 may be implemented as instructions stored in memory (e.g., firmware stored in a memory coupled with the system 100, system 200, and/or wearable ring device 300). For example, the instructions, if executed by a controller (e.g., the memory system controller), may cause the controller to perform the operations of the process flow 600.

In previous wearable devices, the battery may be formed within an aluminum pouch that is manufactured separately from a wearable device, and then the aluminum pouch may be positioned within the wearable device. For example, the battery layers may be deposited within an aluminum pouch, an electrolyte fluid may be injected, and the aluminum pouch may be sealed. The aluminum pouch including the battery may then be integrated into the wearable device. Manufacturing the battery separately from the wearable device may increase manufacturing costs and increase an overall thickness of the wearable device.

By manufacturing the wearable ring device and battery in a step-by-step process as described with reference to process flow 600, the manufacturing and overhead costs may be reduced. For example, the wearable ring device (e.g., including the battery) may be formed by depositing and positioning one layer after the other layer. By manufacturing the cover of the wearable ring device and the battery as a single unit, the manufacturing time may be reduced, thereby reducing the costs associated with manufacturing. In addition, a thinner ring structure may be achieved by utilizing the cover as a structural boundary of the battery rather than separately manufacturing the battery in an enclosure and implementing the enclosure within a wearable device. In such cases, the battery capacity may be increased without increasing an overall thickness of the wearable ring device.

In some wearable devices, the power source (e.g., the battery) of the wearable device may be nondetachable by a user of the wearable device, meaning that the battery is not able to be removed without specialized tools, or without risking damage to the wearable device. In such cases, a user may be unable to swap the battery with a fully charged battery when the energy stored by the battery is depleted, for example. Instead, the user may remove the wearable device from being worn on their body to charge the wearable device such that the wearable device may be unable to acquire physiological data from the user while charging. Additionally, the battery may frequently be the module in a device that declines in performance most quickly (e.g., the battery has a lower lifespan than most other modules of a device). Therefore, when a battery fails or begins to fail, a user may be forced to upgrade to a newer module of the wearable device even though the previous wearable device otherwise operated as intended. In such cases, integrating the battery into the cover may enable the battery to be swapped out when the cover is interchangeable. For example, the battery may be replaceable or exchangeable when integrated into a cover that is removable with respect to the wearable ring device.

At 605, an outer shell of the cover may be formed. For example, the system may form an outer shell component where the outer shell component may include an inner circumferential surface and an outer circumferential surface opposite the inner circumferential surface. In such cases, the outer cover of the wearable ring device may be formed.

At 610, an insulating layer may be deposited. For example, the system may deposit the insulating layer onto the inner circumferential surface of the outer shell component. The wearable ring device may be manufactured by depositing the insulating layer onto the ring outer cover. The insulating layer may be deposited after forming the outer shell component.

At 615, battery layers may be positioned. The system may place the set of anode and cathode layers of the battery of the wearable ring device within a cavity of the inner circumferential surface of the outer shell component. In some cases, the battery layers may be placed within the cavity of the inner circumferential surface after the insulating layer is deposited.

The battery layers may include a set of anode and cathode layers. The wearable ring device may be manufactured by depositing two anode layers and one cathode layer in between the two anode layers. For example, the system may place a first anode layer of the set of anode and cathode layers within the battery chamber and on top of the insulating layer and then place a cathode layer of the set of anode and cathode layers within the battery chamber and on top of the first anode layer. The system may place a second anode layer of the set of anode and cathode layers within the battery chamber and on top of the cathode layer.

In some cases, separator layers may be deposited between the anode and cathode layers. For example, the system may place a first anode layer on top of the insulating layer, deposit a first separator layer on top of the first anode layer, place a first cathode layer on the first separator layer, deposit a second separator layer on top of the first cathode layer, and then place the second anode layer on top of the second separator layer. The separator layer may include one or more holes configured to allow charge carriers (e.g., an electrolyte fluid) to follow between the battery layers. In such cases, the first anode layer may be coupled between the insulating layer and the first separator layer, the first cathode layer may be coupled between the first separator layer and the second separator layer, and the second anode layer may be coupled between the second separator layer and a battery cover layer.

At 620, a battery chamber may be formed. For example, the system may form a battery chamber by coupling a battery cover layer to the inner circumferential surface to form a liquid-tight enclosure that encloses the set of anode and cathode layers within the battery chamber. One or more structural boundaries of the battery chamber are formed by the cavity of the inner circumferential surface and the battery cover layer. The battery cover layer may be an example of an aluminum layer that is positioned on top of the inner circumferential surface to seal a pouch (e.g., form a liquid-tight enclosure) that encloses the battery. The battery chamber may be formed such that the battery extends radially around at least a portion of a circumference of the wearable ring device.

In some examples, the system may couple the battery cover layer to the inner circumferential surface after forming the battery chamber. In some examples, the wearable ring device may be manufactured by depositing the insulator layer around the set of anode and cathode layers. For example, the system may deposit the insulating layer onto the second anode layer, the battery cover layer, or both. In such cases, the insulating layer may be configured to outline the battery chamber and enclose the set of anode and cathode layers of the battery within the battery chamber. The battery cover layer may be coupled to the insulating layer. In some examples, forming the battery chamber may be based on coupling the battery cover layer to the inner circumferential surface.

At 625, one or more holes may be formed in the battery chamber. For example, the system may form a hole within the battery chamber. The hole may be formed on a side of the battery chamber (e.g., at a side of the wearable ring device), at an end of the battery chamber (e.g., when the battery chamber does not extend fully around the circumference of the inner circumferential surface), and other configurations.

At 630, the charge carriers (e.g., electrolyte fluid) may be injected into the battery chamber. For example, the system may inject the charge carriers/electrolyte fluid into the liquid-tight enclosure (e.g., the battery chamber) after forming the hole in the battery chamber. In such cases, the charge carriers may be injected through the hole within the battery chamber. The system may leave a portion of the battery chamber open, via the hole, such that the charge carriers may be injected through the hole.

At 635, a gas may be purged from the battery chamber. Injecting the charge carriers (e.g., electrolyte fluid) through the hole may increase a pressure inside the battery chamber, and/or may introduce additional air or gas into the chamber. In some cases, activating the battery after injecting the charge carriers/electrolyte fluid may generate gas inside the battery chamber, thereby increasing the pressure. In such cases, the gas may be removed from the battery chamber after injecting the charge carriers into the liquid-tight enclosure. The wearable ring device may be manufactured by degassing the battery chamber after injecting the charge carriers. After removing the gas from the battery chamber, the system may seal the hole within the battery chamber.

At 640, a plurality of sensors may be coupled to the battery. For example, the system may couple a PCB to the battery chamber, the inner circumferential surface of the outer shell component, or both. The PCB may be coupled to the battery chamber, the inner circumferential surface of the outer shell component, or both, such that the PCB overlaps with the battery for at least a portion of the circumference of the wearable ring device. In such cases, the PCB is arranged to overlap the battery.

The PCB may include the plurality of sensors configured to acquire physiological data, and the plurality of sensors may be electrically coupled to the battery. In some cases, the plurality of sensors may be positioned on a surface of the PCB opposite of the battery chamber after coupling the PCB to the battery chamber. In such cases, the sensors may face away (e.g., extend away) from the battery components to mitigate temperature effects.

In some cases, a contact element of the PCB may be coupled to battery tabs to electrically couple the plurality of sensors of the PCB to the set of anode and cathode layers of the battery. In such cases, the battery tabs may be electrically coupled to the set of anode and cathode layers and extend from within the battery chamber. For example, the wearable ring device may be manufactured by forming the metal contact on the PCB and the battery tab with the connection ball.

At 645, an inner shell of the cover may be formed. For example, the system may form the inner shell cover after the sensors are coupled to the battery. In such cases, the inner shell of the cover may be formed on top of a cavity that includes the plurality of sensors. The inner shell of the cover may be coupled to the inner circumferential surface, the battery cover layer, or both.

Figure 7:
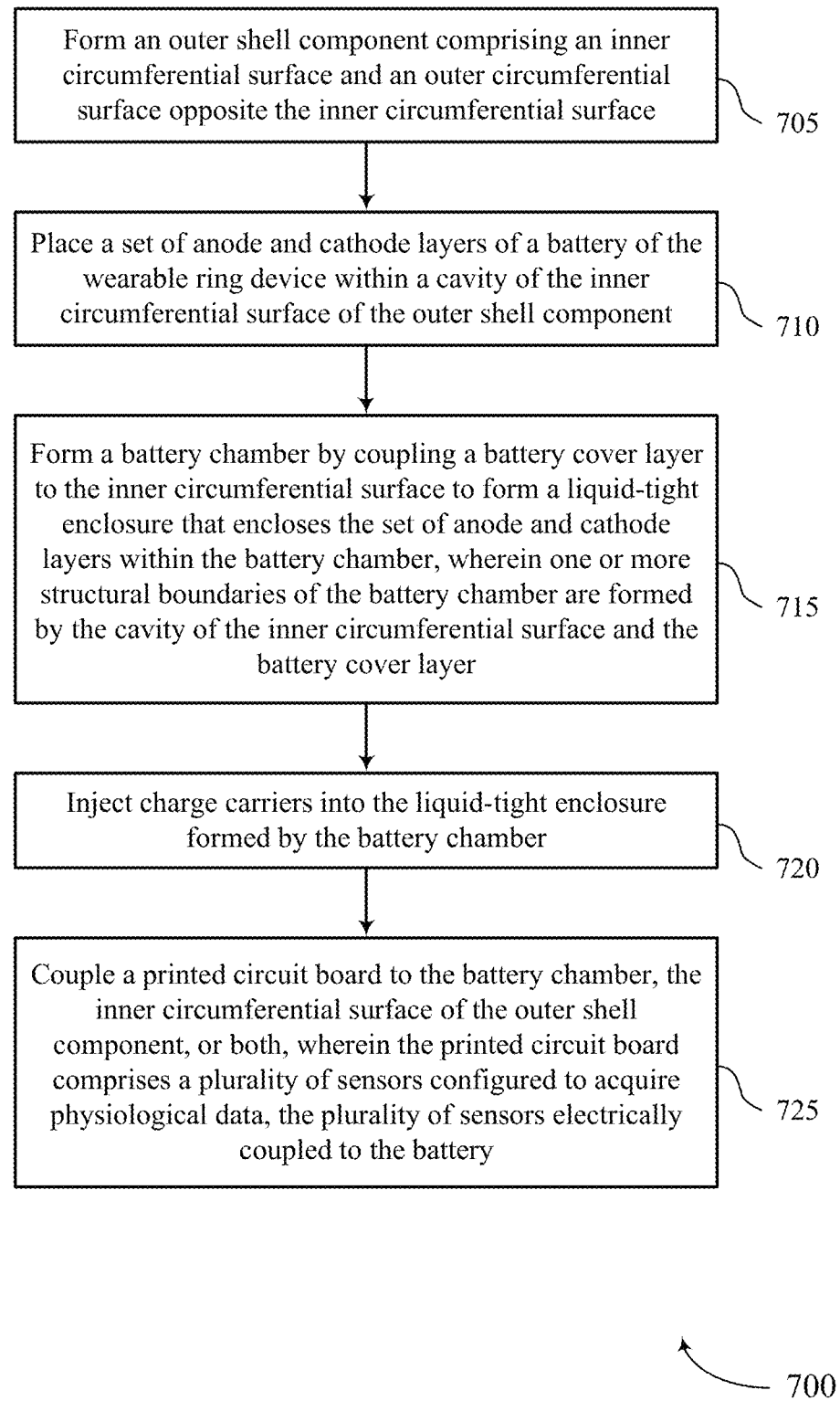
FIG. 7 shows a flowchart illustrating methods that support a wearable ring device with a battery in the cover of the device in accordance with aspects of the present disclosure.

FIG. 7 shows a flowchart illustrating a method 700 that supports a wearable ring device with a battery in the cover of the device in accordance with aspects of the present disclosure. The operations of the method 700 may be implemented by a wearable device or its components as described herein. For example, the operations of the method 700 may be performed by a wearable device as described with reference to FIGS. 1 through 6. In some examples, a wearable device may execute a set of instructions to control the functional elements of the wireless wearable device to perform the described functions. Additionally, or alternatively, the wireless wearable device may perform aspects of the described functions using special-purpose hardware.

At 705, the method may include forming an outer shell component comprising an inner circumferential surface and an outer circumferential surface opposite the inner circumferential surface. The operations of 705 may be performed in accordance with examples as disclosed herein.

At 710, the method may include placing a set of anode and cathode layers of a battery of the wearable ring device within a cavity of the inner circumferential surface of the outer shell component. The operations of 710 may be performed in accordance with examples as disclosed herein.

At 715, the method may include forming a battery chamber by coupling a battery cover layer to the inner circumferential surface to form a liquid-tight enclosure that encloses the set of anode and cathode layers within the battery chamber, wherein one or more structural boundaries of the battery chamber are formed by the cavity of the inner circumferential surface and the battery cover layer. The operations of 715 may be performed in accordance with examples as disclosed herein.

At 720, the method may include injecting charge carriers (e.g., an electrolyte fluid) into the liquid-tight enclosure formed by the battery chamber. The operations of 720 may be performed in accordance with examples as disclosed herein.

At 725, the method may include coupling a PCB to the battery chamber, the inner circumferential surface of the outer shell component, or both, wherein the PCB comprises a plurality of sensors configured to acquire physiological data, the plurality of sensors electrically coupled to the battery. The operations of 725 may be performed in accordance with examples as disclosed herein.

It should be noted that the methods described above describe possible implementations, and that the operations and the steps may be rearranged or otherwise modified and that other implementations are possible. Furthermore, aspects from two or more of the methods may be combined.

An apparatus is described. The apparatus may include an outer shell component comprise an inner circumferential surface and an outer circumferential surface, a battery comprise a set of anode and cathode layers, wherein the battery extends radially around at least a portion of a circumference of the wearable ring device, a battery chamber configure to enclose the set of anode and cathode layers of the battery and an electrolyte fluid, wherein one or more structural boundaries of the battery chamber are formed by a cavity within the inner circumferential surface and a battery cover layer coupled to the inner circumferential surface, wherein the battery chamber forms a liquid-tight enclosure by coupling the battery cover layer to the inner circumferential surface, and a print circuit board comprising a plurality of sensors configured to acquire physiological data, the plurality of sensors electrically coupled to the battery, wherein the PCB overlaps with the battery for at least a second portion of the circumference of the wearable ring device.

In some examples of the apparatus, the apparatus may include an insulating layer configured to outline the one or more structural boundaries of the battery chamber and enclose the set of anode and cathode layers of the battery within the battery chamber, wherein the insulating layer may be coupled to the inner circumferential surface of the outer shell component and the battery cover layer.

In some examples of the apparatus, the apparatus may include a first anode layer on top of the insulating layer, wherein the insulating layer may be disposed between the inner circumferential surface and the first anode layer, a first cathode layer on top of the first anode layer, and a second anode layer on top of the first cathode layer, wherein the insulating layer may be disposed between the second anode layer and the battery cover layer.

In some examples of the apparatus, the insulating layer forms the liquid-tight enclosure by enclosing the set of anode and cathode layers within the battery chamber.

In some examples of the apparatuses, the electrolyte fluid contacts at least a portion of the inner circumferential surface of the outer shell component within the battery chamber.

In some examples of the apparatus, the apparatus may include a plurality of contact elements coupled to the PCB, a plurality of battery tabs electrically coupled to the set of anode and cathode layers, and extending from within the battery chamber, and a plurality of connection elements coupled to the plurality of battery tabs and configured to electrically connect the plurality of battery tabs to the plurality of contact elements of the PCB to electrically couple the plurality of sensors to the battery.

In some examples of the apparatus, the plurality of sensors comprise a light-emitting component, a photodetector, or both, disposed on the PCB at a location within the portion of the circumference of the wearable ring device where the PCB overlaps with the battery.

In some examples of the apparatus, the battery extends radially around an entire portion of the circumference of the wearable ring device.

In some examples of the apparatus, the battery cover layer comprises an aluminum material.

In some examples of the apparatus, the plurality of sensors may be positioned on a surface of the PCB opposite of the battery chamber.

A method is described. The method may include forming an outer shell component comprising an inner circumferential surface and an outer circumferential surface opposite the inner circumferential surface, placing a set of anode and cathode layers of a battery of the wearable ring device within a cavity of the inner circumferential surface of the outer shell component, forming a battery chamber by coupling a battery cover layer to the inner circumferential surface to form a liquid-tight enclosure that encloses the set of anode and cathode layers within the battery chamber, wherein one or more structural boundaries of the battery chamber are formed by the cavity of the inner circumferential surface and the battery cover layer, injecting an electrolyte fluid into the liquid-tight enclosure formed by the battery chamber, and coupling a PCB to the battery chamber, the inner circumferential surface of the outer shell component, or both, wherein the PCB comprises a plurality of sensors configured to acquire physiological data, the plurality of sensors electrically coupled to the battery.

An apparatus is described. The apparatus may include a processor, memory coupled with the processor, and instructions stored in the memory. The instructions may be executable by the processor to cause the apparatus to form an outer shell component comprising an inner circumferential surface and an outer circumferential surface opposite the inner circumferential surface, place a set of anode and cathode layers of a battery of the wearable ring device within a cavity of the inner circumferential surface of the outer shell component, form a battery chamber by coupling a battery cover layer to the inner circumferential surface to form a liquid-tight enclosure that encloses the set of anode and cathode layers within the battery chamber, wherein one or more structural boundaries of the battery chamber are formed by the cavity of the inner circumferential surface and the battery cover layer, inject an electrolyte fluid into the liquid-tight enclosure formed by the battery chamber, and couple a PCB to the battery chamber, the inner circumferential surface of the outer shell component, or both, wherein the PCB comprises a plurality of sensors configured to acquire physiological data, the plurality of sensors electrically coupled to the battery.

Another apparatus is described. The apparatus may include means for forming an outer shell component comprising an inner circumferential surface and an outer circumferential surface opposite the inner circumferential surface, means for placing a set of anode and cathode layers of a battery of the wearable ring device within a cavity of the inner circumferential surface of the outer shell component, means for forming a battery chamber by coupling a battery cover layer to the inner circumferential surface to form a liquid-tight enclosure that encloses the set of anode and cathode layers within the battery chamber, wherein one or more structural boundaries of the battery chamber are formed by the cavity of the inner circumferential surface and the battery cover layer, means for injecting an electrolyte fluid into the liquid-tight enclosure formed by the battery chamber, and means for coupling a PCB to the battery chamber, the inner circumferential surface of the outer shell component, or both, wherein the PCB comprises a plurality of sensors configured to acquire physiological data, the plurality of sensors electrically coupled to the battery.

A non-transitory computer-readable medium storing code is described. The code may include instructions executable by a processor to form an outer shell component comprising an inner circumferential surface and an outer circumferential surface opposite the inner circumferential surface, place a set of anode and cathode layers of a battery of the wearable ring device within a cavity of the inner circumferential surface of the outer shell component, form a battery chamber by coupling a battery cover layer to the inner circumferential surface to form a liquid-tight enclosure that encloses the set of anode and cathode layers within the battery chamber, wherein one or more structural boundaries of the battery chamber are formed by the cavity of the inner circumferential surface and the battery cover layer, inject an electrolyte fluid into the liquid-tight enclosure formed by the battery chamber, and couple a PCB to the battery chamber, the inner circumferential surface of the outer shell component, or both, wherein the PCB comprises a plurality of sensors configured to acquire physiological data, the plurality of sensors electrically coupled to the battery.

Some examples of the method, apparatuses, and non-transitory computer-readable medium described herein may further include operations, features, means, or instructions for depositing an insulating layer onto the inner circumferential surface of the outer shell component prior to placing the set of anode and cathode layers of the battery within the cavity of the inner circumferential surface of the outer shell component.

Some examples of the method, apparatuses, and non-transitory computer-readable medium described herein may further include operations, features, means, or instructions for placing a first anode layer of the set of anode and cathode layers within the battery chamber, and on top of the insulating layer, placing a cathode layer of the set of anode and cathode layers within the battery chamber, and on top of the first anode layer, and placing a second anode layer of the set of anode and cathode layers within the battery chamber, and on top of the cathode layer.

Some examples of the method, apparatuses, and non-transitory computer-readable medium described herein may further include operations, features, means, or instructions for depositing the insulating layer onto the second anode layer, the battery cover layer, or both and coupling the battery cover layer to the inner circumferential surface, wherein the insulating layer may be configured to outline the battery chamber and enclose the set of anode and cathode layers of the battery within the battery chamber, and wherein forming the battery chamber may be based at least in part on coupling the battery cover layer to the inner circumferential surface.

In some examples of the method, apparatuses, and non-transitory computer-readable medium described herein, the battery chamber may be formed such that the battery extends radially around at least a portion of a circumference of the wearable ring device.

In some examples of the method, apparatuses, and non-transitory computer-readable medium described herein, the PCB may be coupled to the battery chamber, the inner circumferential surface of the outer shell component, or both, such that the PCB overlaps with the battery for at least a second portion of the circumference of the wearable ring device.

Some examples of the method, apparatuses, and non-transitory computer-readable medium described herein may further include operations, features, means, or instructions for coupling a plurality of contact elements of the PCB to a plurality of battery tabs to electrically couple the plurality of sensors of the PCB to the set of anode and cathode layers of the battery, wherein the plurality of battery tabs may be electrically coupled to the set of anode and cathode layers, and extend from within the battery chamber.

Some examples of the method, apparatuses, and non-transitory computer-readable medium described herein may further include operations, features, means, or instructions for forming a hole within the battery chamber, wherein the electrolyte fluid may be injected through the hole within the battery chamber.

Some examples of the method, apparatuses, and non-transitory computer-readable medium described herein may further include operations, features, means, or instructions for removing a gas from the battery chamber based at least in part on injecting the electrolyte fluid into the liquid-tight enclosure and sealing the hole within the battery chamber based at least in part on removing the gas.

Some examples of the method, apparatuses, and non-transitory computer-readable medium described herein may further include operations, features, means, or instructions for positioning the plurality of sensors on a surface of the PCB opposite of the battery chamber based at least in part on coupling the PCB to the battery chamber.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a DSP, an ASIC, an FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration).

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media can comprise RAM, ROM, electrically erasable programmable ROM (EEPROM), compact disk (CD) ROM or other optical disk storage, magnetic disk storage or other magnetic storage devices, or any other non-transitory medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

What is claimed is:

1. A wearable ring device, comprising:
an outer shell component comprising an inner circumferential surface and an outer circumferential surface;
a battery comprising a set of anode and cathode layers, wherein the battery extends radially around at least a portion of a circumference of the wearable ring device;
a battery chamber configured to enclose the set of anode and cathode layers of the battery and charge carriers, wherein one or more structural boundaries of the battery chamber are formed by a cavity within the inner circumferential surface and a battery cover layer coupled to the inner circumferential surface, wherein the battery chamber forms a liquid-tight enclosure by coupling the battery cover layer to the inner circumferential surface; and
a printed circuit board comprising a plurality of sensors configured to acquire physiological data, the plurality of sensors electrically coupled to the battery, wherein the printed circuit board overlaps with the battery for at least a second portion of the circumference of the wearable ring device.

2. The wearable ring device of claim 1, further comprising:
an insulating layer configured to outline the one or more structural boundaries of the battery chamber and enclose the set of anode and cathode layers of the battery within the battery chamber, wherein the insulating layer is coupled to the inner circumferential surface of the outer shell component and the battery cover layer.

3. The wearable ring device of claim 2, wherein the set of anode and cathode layers further comprise:
a first anode layer on top of the insulating layer, wherein the insulating layer is disposed between the inner circumferential surface and the first anode layer;
a first cathode layer on top of the first anode layer; and
a second anode layer on top of the first cathode layer, wherein the insulating layer is disposed between the second anode layer and the battery cover layer.

4. The wearable ring device of claim 2, wherein the insulating layer forms the liquid-tight enclosure by enclosing the set of anode and cathode layers within the battery chamber.

5. The wearable ring device of claim 1, wherein the charge carriers contact at least a portion of the inner circumferential surface of the outer shell component within the battery chamber.

6. The wearable ring device of claim 1, further comprising:
a plurality of contact elements coupled to the printed circuit board;
a plurality of battery tabs electrically coupled to the set of anode and cathode layers, and extending from within the battery chamber; and
a plurality of connection elements coupled to the plurality of battery tabs and configured to electrically connect the plurality of battery tabs to the plurality of contact elements of the printed circuit board to electrically couple the plurality of sensors to the battery.

7. The wearable ring device of claim 1, wherein the plurality of sensors comprise a light-emitting component, a photodetector, or both, disposed on the printed circuit board at a location within the portion of the circumference of the wearable ring device where the printed circuit board overlaps with the battery.

8. The wearable ring device of claim 1, wherein the battery extends radially around an entire portion of the circumference of the wearable ring device.

9. The wearable ring device of claim 1, wherein the battery cover layer comprises an aluminum material.

10. The wearable ring device of claim 1, wherein the plurality of sensors are positioned on a surface of the printed circuit board opposite of the battery chamber.

11. A method for manufacturing a wearable ring device, comprising:
forming an outer shell component comprising an inner circumferential surface and an outer circumferential surface opposite the inner circumferential surface;
placing a set of anode and cathode layers of a battery of the wearable ring device within a cavity of the inner circumferential surface of the outer shell component;
forming a battery chamber by coupling a battery cover layer to the inner circumferential surface to form a liquid-tight enclosure that encloses the set of anode and cathode layers within the battery chamber, wherein one or more structural boundaries of the battery chamber are formed by the cavity of the inner circumferential surface and the battery cover layer;
injecting charge carriers into the liquid-tight enclosure formed by the battery chamber; and
coupling a printed circuit board to the battery chamber, the inner circumferential surface of the outer shell component, or both, wherein the printed circuit board comprises a plurality of sensors configured to acquire physiological data, the plurality of sensors electrically coupled to the battery.

12. The method of claim 11, further comprising:
depositing an insulating layer onto the inner circumferential surface of the outer shell component prior to placing the set of anode and cathode layers of the battery within the cavity of the inner circumferential surface of the outer shell component.

13. The method of claim 12, further comprising:
placing a first anode layer of the set of anode and cathode layers within the battery chamber, and on top of the insulating layer;
placing a cathode layer of the set of anode and cathode layers within the battery chamber, and on top of the first anode layer; and
placing a second anode layer of the set of anode and cathode layers within the battery chamber, and on top of the cathode layer.

14. The method of claim 13, further comprising:
depositing the insulating layer onto the second anode layer, the battery cover layer, or both; and
coupling the battery cover layer to the inner circumferential surface, wherein the insulating layer is configured to outline the battery chamber and enclose the set of anode and cathode layers of the battery within the battery chamber, and wherein forming the battery chamber is based at least in part on coupling the battery cover layer to the inner circumferential surface.

15. The method of claim 11, wherein the battery chamber is formed such that the battery extends radially around at least a portion of a circumference of the wearable ring device.

16. The method of claim 15, wherein the printed circuit board is coupled to the battery chamber, the inner circumferential surface of the outer shell component, or both, such that the printed circuit board overlaps with the battery for at least a second portion of the circumference of the wearable ring device.

17. The method of claim 11, further comprising:
coupling a plurality of contact elements of the printed circuit board to a plurality of battery tabs to electrically couple the plurality of sensors of the printed circuit board to the set of anode and cathode layers of the battery, wherein the plurality of battery tabs are electrically coupled to the set of anode and cathode layers, and extend from within the battery chamber.

18. The method of claim 11, further comprising:
forming a hole within the battery chamber, wherein the charge carriers are injected through the hole within the battery chamber.

19. The method of claim 18, further comprising:
removing a gas from the battery chamber based at least in part on injecting the charge carriers into the liquid-tight enclosure; and
sealing the hole within the battery chamber based at least in part on removing the gas.

20. The method of claim 11, further comprising:
positioning the plurality of sensors on a surface of the printed circuit board opposite of the battery chamber based at least in part on coupling the printed circuit board to the battery chamber.

\* \* \* \* \*